(12) United States Patent
Ni Ghriallais et al.

(10) Patent No.: US 11,602,621 B2
(45) Date of Patent: Mar. 14, 2023

(54) DEVICE FOR CONTROLLABLY DEPLOYING EXPANDABLE IMPLANTS

(71) Applicant: ProVerum Limited, Dublin (IE)

(72) Inventors: Riona Ni Ghriallais, Dublin (IE); Conor Harkin, Dublin (IE)

(73) Assignee: ProVerum Limited, Dublin (IE)

( * ) Notice: Subject to any disclaimer, the term of this patent is extended or adjusted under 35 U.S.C. 154(b) by 0 days.

(21) Appl. No.: 17/663,812

(22) Filed: May 17, 2022

(65) Prior Publication Data

US 2022/0273918 A1    Sep. 1, 2022

Related U.S. Application Data

(63) Continuation of application No. PCT/EP2020/083102, filed on Nov. 23, 2020, which is a continuation-in-part of application No. 16/692,347, filed on Nov. 22, 2019, now Pat. No. 11,273,025.

(30) Foreign Application Priority Data

Nov. 22, 2019    (GB) ...................... 1917087

(51) Int. Cl.
*A61M 29/00* (2006.01)
*A61B 1/307* (2006.01)
*A61B 1/00* (2006.01)
*A61F 2/00* (2006.01)

(52) U.S. Cl.
CPC ......... *A61M 29/00* (2013.01); *A61B 1/00087* (2013.01); *A61B 1/00135* (2013.01); *A61B 1/307* (2013.01); *A61F 2/00* (2013.01)

(58) Field of Classification Search
CPC .......... A61M 29/00; A61M 2025/0681; A61B 1/307; A61B 17/3468; A61B 2017/00367; A61F 2/04; A61F 2/966
See application file for complete search history.

(56) References Cited

U.S. PATENT DOCUMENTS

| 4,580,568 A | 4/1986 | Gianturco |
| 4,830,003 A | 5/1989 | Wolff et al. |
| 5,035,706 A | 7/1991 | Giantureo et al. |

(Continued)

FOREIGN PATENT DOCUMENTS

| BE | 892016 | 5/1982 |
| BE | 1015962 | 12/2005 |

(Continued)

OTHER PUBLICATIONS

International Search Report and Written Opinion issued in PCT Application No. PCT/EP2020/083102, dated Mar. 9, 2021.

*Primary Examiner* — Tasnim Mehjabin Ahmed
(74) *Attorney, Agent, or Firm* — Knobbe Martens Olson & Bear LLP

(57) ABSTRACT

Aspects of the present invention relate to a delivery device for locating an expandable implant for treating BPH within the prostatic urethra of a patient. The delivery device comprises an inner tube and an outer sleeve movable relative to the inner tube between a stored position and a deployed position. The outer sleeve surrounds the inner tube to define an annulus therebetween and the expandable implant is retained within the annulus when the outer sleeve is in the stored position.

34 Claims, 31 Drawing Sheets

(56) References Cited

U.S. PATENT DOCUMENTS

| | | | |
|---|---|---|---|
| 5,159,920 A | 11/1992 | Condon et al. |
| 5,269,802 A | 12/1993 | Garber |
| 5,292,331 A | 3/1994 | Boneau |
| 5,591,277 A | 1/1997 | Braunheim |
| 5,599,325 A | 2/1997 | Ju et al. |
| 5,674,278 A | 10/1997 | Boneau |
| 5,697,967 A | 12/1997 | Dinh et al. |
| 5,782,838 A | 7/1998 | Beyar et al. |
| 5,830,179 A | 11/1998 | Mikus et al. |
| 6,093,194 A | 7/2000 | Mikus et al. |
| 6,110,199 A | 8/2000 | Walak |
| 6,395,017 B1 * | 5/2002 | Dwyer .................... A61F 2/966 |
| | | | 623/1.11 |
| 6,929,663 B2 | 8/2005 | Rioux et al. |
| 7,112,226 B2 | 9/2006 | Gellman |
| 8,591,569 B2 | 11/2013 | Shin et al. |
| 8,603,187 B2 | 12/2013 | Kilemnik et al. |
| 9,005,183 B2 | 4/2015 | Harkins, Jr. |
| 9,114,039 B2 | 8/2015 | Jordan et al. |
| 9,333,102 B2 | 5/2016 | Yachia et al. |
| 9,848,905 B2 | 12/2017 | Kilemnik |
| 9,968,479 B2 | 5/2018 | Harkins, Jr. |
| 10,004,584 B2 | 6/2018 | Bartning et al. |
| 10,035,005 B2 | 7/2018 | Bar-On et al. |
| 10,058,718 B2 | 8/2018 | Sethuraman et al. |
| 10,478,283 B2 | 11/2019 | Bachar |
| 10,507,122 B2 | 12/2019 | Bachar |
| 10,682,245 B2 | 6/2020 | Harkin et al. |
| 10,881,539 B2 | 1/2021 | Harkin et al. |
| 11,027,106 B2 | 6/2021 | Bachar |
| 11,241,312 B2 | 2/2022 | Simonin |
| 11,273,025 B2 | 3/2022 | Ni Ghriallais et al. |
| 2002/0156394 A1 | 10/2002 | Mehrotra et al. |
| 2006/0100688 A1 | 5/2006 | Jordan et al. |
| 2006/0136031 A1 | 6/2006 | Gallo et al. |
| 2007/0077266 A1 | 4/2007 | Egashira |
| 2007/0163668 A1 | 7/2007 | Arbefeuille et al. |
| 2009/0171442 A1 | 7/2009 | Young et al. |
| 2009/0210045 A1 | 8/2009 | Sorensen et al. |
| 2009/0312667 A1 | 12/2009 | Utsunomiya et al. |
| 2010/0137893 A1 | 6/2010 | Kilemnick et al. |
| 2010/0152835 A1 | 6/2010 | Orr |
| 2011/0301690 A1 | 12/2011 | Giasolli |
| 2012/0179086 A1 | 7/2012 | Shank |
| 2012/0290065 A1 | 11/2012 | Li et al. |
| 2014/0012192 A1 | 1/2014 | Bar-On et al. |
| 2014/0188249 A1 | 7/2014 | Pendleton et al. |
| 2014/0257020 A1 | 9/2014 | Smith et al. |
| 2015/0257908 A1 | 9/2015 | Chao et al. |
| 2015/0374408 A1 | 12/2015 | Ogdahl et al. |
| 2016/0007987 A1 | 1/2016 | Catanese, III et al. |
| 2016/0262862 A1 | 9/2016 | Fischer |
| 2016/0317180 A1 | 11/2016 | Kilemnik |
| 2017/0135830 A1 * | 5/2017 | Harkin .................... A61F 2/86 |
| 2017/0165062 A1 | 6/2017 | Rothstein |
| 2018/0028222 A1 | 2/2018 | Kilemnik |
| 2018/0235651 A1 | 8/2018 | Kilemnik |
| 2018/0280669 A1 | 10/2018 | Shlomovitz et al. |
| 2018/0318114 A1 | 11/2018 | Huang et al. |
| 2018/0325705 A1 | 11/2018 | Harkin et al. |
| 2018/0344995 A1 | 12/2018 | Bar-On et al. |
| 2019/0295444 A1 | 9/2019 | Zunke et al. |
| 2019/0298334 A1 | 10/2019 | Catanese, III et al. |
| 2020/0022692 A1 | 1/2020 | Lamson et al. |
| 2020/0315823 A1 | 10/2020 | Harkin et al. |
| 2021/0022594 A1 | 1/2021 | Jen et al. |
| 2021/0052854 A1 | 2/2021 | Tavallaei et al. |
| 2021/0059704 A1 | 3/2021 | Kilemnik |
| 2021/0100666 A1 | 4/2021 | Harkin et al. |
| 2021/0106730 A1 | 4/2021 | Koroschetz et al. |
| 2021/0145619 A1 | 5/2021 | Bly et al. |
| 2021/0154000 A1 | 5/2021 | Ni Ghriallais et al. |
| 2021/0161642 A1 | 6/2021 | Jen et al. |
| 2021/0259799 A1 | 8/2021 | Lessard et al. |
| 2021/0290917 A1 | 9/2021 | Bachar |
| 2022/0054184 A9 | 2/2022 | Rajagopalan et al. |
| 2022/0079613 A1 | 3/2022 | Aljuri et al. |
| 2022/0192813 A1 | 6/2022 | Ni Ghriallais et al. |

FOREIGN PATENT DOCUMENTS

| | | |
|---|---|---|
| CN | 101945621 | 1/2011 |
| CN | 202822454 | 3/2013 |
| EP | 1 420 720 | 9/2007 |
| EP | 1 599 153 | 11/2010 |
| EP | 1 959 876 | 9/2011 |
| EP | 1 827 305 | 1/2012 |
| EP | 2 446 855 | 5/2012 |
| EP | 2 316 392 | 1/2013 |
| EP | 3 167 845 | 5/2017 |
| EP | 3 328 317 | 6/2018 |
| EP | 3 415 121 | 12/2018 |
| EP | 2 685 933 | 2/2019 |
| EP | 3 089 780 | 9/2019 |
| EP | 3 597 148 | 1/2020 |
| EP | 3 610 831 | 2/2020 |
| EP | 3 096 711 | 3/2021 |
| EP | 3 831 342 | 6/2021 |
| FR | 2586185 | 2/1987 |
| JP | 51-51894 | 5/1976 |
| JP | 2005-261686 | 9/2005 |
| WO | WO 90/13332 | 11/1990 |
| WO | WO 2011/002779 | 1/2011 |
| WO | WO 2011/021779 | 2/2011 |
| WO | WO 2015/101975 | 7/2015 |
| WO | WO 2015/111063 | 7/2015 |
| WO | WO 2015/138763 | 9/2015 |
| WO | WO 2017/081326 | 5/2017 |
| WO | WO 2021/113340 | 6/2021 |

* cited by examiner

DEVICE FOR CONTROLLABLY DEPLOYING EXPANDABLE IMPLANTS

CROSS-REFERENCE TO RELATED APPLICATIONS

This application is a continuation of PCT App. No. PCT/EP2020/083102, filed on Nov. 23, 2020, which is hereby incorporated by reference in its entirety, and which PCT App. No. PCT/EP2020/083102 is a continuation in part of U.S. patent application Ser. No. 16/692,347, filed on Nov. 22, 2019 issued as U.S. Pat. No. 11,273,025 on Mar. 15, 2022, and which PCT App. No. PCT/EP2020/083102 claims priority to UKIPO App. No. GB 201917087.7, filed on Nov. 22, 2019.

TECHNICAL FIELD

The present disclosure relates to a delivery device for an expandable implant and to a method for using such a device. In particular, but not exclusively, such an implant may be located within the prostatic urethra of a patient to treat benign prostatic hyperplasia (BPH). Aspects of the invention therefore relate to a delivery device for locating an expandable implant for treating BPH within the prostatic urethra and to a method of delivering or deploying such an implant.

BACKGROUND

BPH is a noncancerous disease that results in enlargement of the prostate. The prostate surrounds a section of the urethra adjoining the bladder, namely the prostatic urethra. Thus, as the prostate expands, it may press inwardly against and place pressure on the prostatic urethra and the neck of the bladder and so make it difficult to pass urine out of the bladder.

It is known to treat BPH in various ways including ongoing medication or, in particularly bad cases, surgery. However, both of these approaches are undesirable. For example, in the US alone more, than $5 billion is spent annually on medication to manage BPH. Furthermore, surgical solutions can be particularly invasive and uncomfortable for the patient. Consequently, there has been a move in the art toward the use of expandable implants or stents that can be inserted into the urethra to react against, and hence to alleviate, the inward pressure applied to the urethra and bladder neck by the enlarged prostate.

Expandable implants provide a minimally invasive and low-cost solution for treating BPH. However, locating the implant in the correct position within the urethra is challenging for a clinician. If the implant is deployed incorrectly, it may not provide adequate symptom relief, may fail due to migration or excessive encrustation and may be challenging and invasive to recover the deployed expander from the patient's body.

An example of an expandable implant, or expander, for treating BPH is disclosed in WO 2017/081326. The expander of WO 2017/081326 is designed to be positioned within the prostatic urethra of a patient between the bladder neck and external sphincter and then to expand laterally. The expander thereby applies a radially-outward force on the surrounding walls of the prostatic urethra to alleviate the symptoms of BPH.

Positioning the expander correctly within the prostatic urethra is challenging for a clinician as the expander must be positioned accurately both in a longitudinal direction and circumferentially or angularly. For example, the expander should be positioned longitudinally at a position between the bladder neck and the external sphincter and should also be oriented so as to engage the three lobes of the prostate. If the expander is deployed in an incorrect position, for example by being deployed accidentally or prematurely, then a complex procedure may be required to remove or reposition the expander. As a result, there is a need for a minimally-invasive delivery device that allows a clinician accurately to position and deploy an expandable implant within the prostatic urethra of a patient.

WO 2017/081326 describes a delivery device for delivering an expander to a target site within a body lumen such as the prostatic urethra. The delivery device comprises an ejection element with a triangular cross-section configured to engage and support the expander. The delivery device may be inserted into the urethra through the penis and advanced along the urethra to the target site. When the clinician is satisfied that the expander is in the correct position, the ejection element is advanced distally so that the expander is ejected from the delivery device.

Even with the assistance of the delivery device of WO 2017/081326, it can be challenging to position the expander reliably and accurately within a patient's prostatic urethra. For example, advancing the ejection element could cause the expander to spring or jump forward upon deployment, thereby making it difficult to position the expander accurately within the prostatic urethra, both longitudinally and circumferentially. Relying on the expander simply to self-locate relative to the anatomy by virtue of its expansion can be unreliable and unpredictable.

Furthermore, a single-step delivery device such as that described in WO 2017/081326 can be susceptible to accidental deployment. Also, the device does not allow a clinician to pause or to reverse deployment of the expander if the clinician determines that the expander is not being positioned accurately within the target site.

U.S. Pat. No. 6,093,194 to Mikus et al discloses a stent delivery catheter that comprises outer and inner sheaths and an endoscope serving as an imaging component within the stent. Provision is made to orient the stent on the inner sheath. However, the positioning of the endoscope relative to the sheaths and the stent does not facilitate effective imaging throughout the stent delivery process.

U.S. Pat. No. 6,033,413, also to Mikus at al, discloses a stent delivery system for use with shape memory stents, in which stent expansion occurs when the stent is heated above the austenite transition temperature. A catheter includes a warming fluid system in which an endoscope used in the procedure can act as a fluid supply line and as a valve to control the flow of warming fluid to the stent. However, this complex system does not address the challenges of accurately and reliably positioning the stent.

US 2005/0278010 to Richardson discloses a stent delivery system with fibre-optic imaging capability. Similarly, U.S. Pat. No. 5,749,848 to Jang et al discloses a catheter system having imaging, balloon angioplasty and capability for guided stent deployment. In each case, the relative positions of the imaging system and the implant do not provide for effective imaging throughout the delivery process.

U.S. Pat. No. 8,467,854 to Lewis et al, discloses a neurovascular intervention device that, like Richardson and Jang et al above, does not provide for effective imaging throughout the delivery process due to the relative positions of the imaging system and a treatment device that can deliver an implant such as a stent. Indeed, simultaneous deployment and imaging may not be possible.

U.S. Pat. No. 6,926,732 to Derus et al discloses a stent delivery device and method at is said to be usable for various procedures, including treatment of BPH. The stent is located in a casing member for positioning and delivery but that casing member would block the view of the anatomy available through an imaging system of the device. In particular, the anatomy cannot be viewed relative to or in line with the distal end of the stent or from inside the stent. Consequently, if the device is used to treat BPH, the imaging system could merely locate the prostatic urethra but could not define and indicate specific alignment of the stent with anatomical features.

US 2012/283816 to Jordan et al discloses systems for delivering and deploying self-expanding stents that incorporate mechanisms for retrieving partially-deployed stents. US 2020/113719 to Desrosiers also provides for recapture of a partially-deployed implant. US 2011/301685 to Kao discloses a bi-directional stent delivery system. EP 2745813 to Roeder discloses an endoluminal stent on a guide wire. In each case; no effective provision is made for imaging the stent delivery location throughout the delivery process, and release and positioning of the stent may be unreliable.

It is an aim of the present invention to address one or more of the disadvantages associated with the prior art.

SUMMARY OF THE INVENTION

In general terms, the invention provides a delivery device for imaging and locating an expandable implant within the prostatic urethra of a patient when treating BPH. The delivery device comprises: an inner tube or other elongate element such as a rod; a tubular outer sleeve movable relative to the inner tube between a storage position and a deployed position; and an imaging device.

The outer sleeve surrounds the inner tube to define an annulus between them. The expandable implant is retained within the annulus when the outer sleeve is in the storage position. In the storage position, the outer sleeve at least partially surrounds the expandable implant such that the implant is retained on the inner tube. Thus, when in the storage position, the outer sleeve prevents the expandable implant expanding radially. Conversely, in the deployed position, the expander is uncovered by the outer sleeve to allow the expander to expand radially.

In the storage position, the imaging device allows a clinician to view the expander relative to the anatomy thereby making it easier for the clinician to align the expander correctly relative to the anatomy before releasing the expander from the device. The imaging device may be movable longitudinally relative to the outer sleeve and/or the inner tube or may be fixed against longitudinal movement relative to the outer sleeve and/or the inner tube. For example, the outer sleeve and the imaging device may be movable together relative to the inner tube between the storage position and the deployed position.

Broadly, the invention resides in a delivery device for deploying a self-expanding implant within a body cavity. The device comprises: at least one retention formation for holding the implant against axial or circumferential movement; an elongate longitudinally-extending outer element, radially outboard of the or each retention formation; and an imaging head disposed on a longitudinal axis that extends on a radially-inboard side of the or each retention formation.

The outer element is movable longitudinally relative to the or each retention formation, between: a storage position in which the outer element surrounds the implant and holds the implant engaged with, or prevents the implant disengaging from, the or each retention formation; and a partial-deployment position in which the outer element uncovers a distal portion of the implant while surrounding a proximal portion of the implant to continue holding the implant engaged with the or each retention formation.

Also, the imaging head is retractable proximally between: an advanced position when the outer element is in the storage position; and a retracted position when the outer element is in the partial-deployment position. The imaging head may be configured to define a field of view extending from a viewpoint that is radially inboard with respect to the or each retention formation and hence also inboard with respect to the implant.

The outer element may also be movable longitudinally, relative to the or each retention formation, into a full-deployment position in which the outer element uncovers the proximal portion of the implant to an extent sufficient to disengage the implant from the retention formation for radial self-expansion within the body cavity.

According to an aspect of the present invention there is provided a delivery device for locating an expandable implant for treating BPH within the prostatic urethra of a patient. A delivery tube of the delivery device comprises: a first elongate element that comprises or supports an imaging device; and a second elongate element surrounding the first elongate element to define an annulus therebetween; wherein the second elongate element is retractable relative to the first elongate element, between: a storage position in which the second elongate element is configured to surround the implant thereby retaining the implant within the annulus; a partially-deployed position in which the second elongate element is configured to partially uncover the implant; and a fully-deployed position in which the second elongate element is configured to uncover the implant to an extent sufficient to allow the implant to expand radially within the prostatic urethra.

When in the storage position, the distal image-receiving face of the imaging device may be locked at or near the distal extremity of the delivery device. This allows a clinician to view the anatomy, preferably with an uninterrupted field of view. When in the partially-deployed position, the distal face of the imaging device may be positioned within the interior of the expander, at a location that is proximal relative to the distal tip of the expander. This allows the clinician to view a distal portion of the expander relative to the anatomy, thereby making it easier for the clinician to align the expander relative to the anatomy.

The first elongate element may be, for example, an inner tube or rod and the second elongate element may be an outer sleeve or tube. The first and second elongate elements may be elliptical, for example circular, in cross-section and are preferably cylindrical.

The delivery device of the invention beneficially provides for accurate positioning and deployment of an expandable implant for treating BPH within the prostatic urethra of a patient. The outer sleeve may retain the expandable implant or expander within the annulus by surrounding the expander and preventing radial expansion of the expander until the expander is correctly located within the prostatic urethra.

In an embodiment, when in the partially-deployed position, a distal tip of the outer element, and a distal tip or face of the imaging device, may be positioned proximally with respect to a distal tip of the inner element. Beneficially, the partially-deployed position uncovers a portion of the expander while still retaining the expander in a compressed or stored configuration on the inner element. This allows a clinician to view the expander relative to the anatomy thereby making it easier for a clinician to align the expander relative to the anatomy. Furthermore, moving the outer element from the intermediate partially-deployed position to the fully-deployed position involves a smaller longitudinal movement than from the storage position to the fully-deployed position. This improves the accuracy of deployment of the expander.

In one embodiment, the delivery device may comprise a third elongate element located between the first, inner elongate element and the second, outer elongate element. The third elongate element may an intermediate tube such as a steering tube.

The delivery device may comprise one or more retention features for inhibiting movement of the expander. The retention feature advantageously retains the expandable implant relative to the inner tube of the intermediate tube within the annulus. This beneficially prevents longitudinal or angular movement of the expander relative to the inner tube or steering tube prior to deployment of the expander, in an embodiment, the retention feature may be located within the annulus.

In one embodiment the outer sleeve may surround the retention feature when in the partially-deployed position or in the storage position. This prevents radial expansion of the expander prior to full deployment of the expander. Furthermore, the outer sleeve may be returned from the partially-deployed position to the storage position if the clinician wishes to abort or pause deployment of the expander.

The retention feature may, for example, comprise at least one protrusion on the inner element. In an embodiment, the retention feature comprises a proximal protrusion and a distal protrusion located on the inner element. A slot for at least partially receiving the expander may be defined between the distal protrusion and the proximal protrusion. The expander may be received within the slot. For example, the expander may comprise an apex and one of the protrusions may be located between opposing sides of the apex when the expander is located on the inner element.

The inner element may comprise two, three or more sets of retention features spaced angularly and/or longitudinally that are configured to engage and retain the expander in another embodiment the protrusions may be located on or extending distally from an intermediate tube. The protrusions may be oriented on the inner element or intermediate tube such that the expander is orientated substantially correctly when the delivery device is inserted into the urethra in an upright or otherwise known or predetermined orientation.

A gap may be defined between a top or radially outer surface of a retention feature and a radially inner surface of the outer sleeve when the outer sleeve is in the storage position or in the partially-deployed position. The gap is narrower than a radial thickness of a part of the expander to be engaged by the retention feature. For example, the delivery device the expander may comprise a wire retained by the retention feature and the gap may be smaller than the thickness of the wire. The gap beneficially provides clearance between the retention feature and the outer sleeve to allow the outer sleeve to move freely relative to the inner tube. Furthermore, the gap may allow fluids to flow along the annulus if the annulus forms part of an irrigation channel.

The delivery device may further comprise a handle connected to a proximal end of the inner and/or outer elements to allow the delivery device to be held and gripped by a clinician. Furthermore, the handle may be operable to move the outer sleeve and the imaging device between a storage position, a fully-deployed position and a partially-deployed position.

In an embodiment, the handle may comprise a proximal grip and a distal grip. In another embodiment, the handle may comprise a two or three finger power grip, similar to that of an endoscope, in which the middle and or ring and little fingers hold the endoscope handle and the index and or middle fingers operate a steering and other mechanisms.

The handle may comprise a lever, catch or other latch that is movable between a locked position and an unlocked position to serve as a detent. When the latch is in the locked position, the outer element is locked in the storage position. The latch may be movable into an intermediate position and when the lever is in that position, the outer sleeve can be moved from the storage position to the partially-deployed position. The latch may also be movable into a fully-deployed position. When the latch is in the fully-deployed position, the outer element can be moved between the partially-deployed position and the fully-deployed position.

When the expander is retained within the annulus in use, a distal end of the inner element may be located distally or in longitudinal alignment with respect to a distal end of the expander. Alternatively, a distal end of the inner element may be located proximally with respect to a distal end of the expander and distally with respect to a proximal end of the expander.

Beneficially, the inner element provides support to the expander when the expander is retained on the inner element, such that longitudinal struts of the expander are maintained in generally parallel relation when the expander is in the stored configuration. This advantageously promotes radial expansion of the expander during deployment and further reduces the possibility of the expander becoming dislodged from the retention features. Furthermore, the inner element supports the expander when the delivery tube is being inserted into, and along, the urethra. This beneficially prevents the expander being compressed further by the urethra, which could otherwise cause the expander to disengage from the retention features.

The inner element may comprise an inner lumen that may extend along the length of the inner tube. Furthermore, the inner lumen may act as an irrigation channel for clearing the field of view and draining fluids from the bladder and/or the urethra. The imaging device may be at least partially received within the inner lumen, or the inner element may be an imaging device. The imaging device may comprise an imaging chip or fibre optics or the imaging device may comprise a telescope. For example, an imaging chip may be connected to an image display device and wires connecting the imaging device to the image display device and a power source may run through the inner lumen. The imaging device may be in a fixed circumferential position relative to the inner element that retains the expander such that the imaging device cannot rotate, hence facilitating accurate longitudinal and angular alignment of the implant with the anatomy.

In the storage configuration, all or most of the expander may be positioned proximally relative to, and hence outside, the field of view of the imaging device. This is beneficial as the imaging device may generate images of the patient's anatomy to allow the clinician to assess the anatomy prior to the deployment of the expander. However, the field of view of the imaging device may include at least a portion of the expander when the expander is in its stored configuration on the inner tube. The viewpoint, being the origin of the field of view of the imaging device, may be from the inner side of the expander. This is beneficial as the imaging device can then receive images of the expander relative to the anatomy of the patient. This allows the clinician to locate and position the expandable implant accurately relative to the anatomy by using the images from the imaging device.

The imaging device may, for example, be movable relative to the inner element but may be fixed relative to the outer element. As such, the imaging device may be moved relative to the inner element when the outer sleeve is moved between the storage, partially-deployed and fully-deployed positions. In an embodiment the imaging device may be fixed relative to the inner and outer elements in such a way that it cannot rotate circumferentially about a central longitudinal axis of the delivery tube. This allows a clinician to locate the expandable implant accurately in a certain axial position relative to the anatomy without rotational movement, ensuring precise deployment.

In another embodiment, the inner element, and optionally the imaging device, is movable longitudinally relative to an intermediate tube between a distally-advanced position and a proximally-retracted position. A distal tip of the inner element may be positioned distally with respect to the distal tip of the outer element when the inner tube is in the distally advanced position. The outer element may be outside a field of view of the imaging device when the inner element is in the distally-advanced position. The imaging device may, however, be configured such that its field of view captures at least a distal portion of the expander when the inner element is in the proximally-retracted position.

The outer element may comprise graduation marks spaced at longitudinal to provide a visual aid to the clinician when positioning the expander in the desired longitudinal position. The graduation marks could, however, be on the inner element if the outer element is transparent such that the graduation marks on the inner element are visible to the clinician.

In an embodiment, the delivery device may comprise an expandable implant. The implant may be supported by the first elongate element and at least partially covered by the second elongate element.

The inventive concept extends to a method of deploying a self-expanding implant within a patient's body cavity. The method comprises: inserting an elongate delivery sheath of an implant delivery system into the cavity with an imaging head of the delivery system in a distally-advanced position and with the delivery sheath in a storage position in which the implant is retained within and covered by the delivery sheath; navigating the implant to a target site within the cavity, guided by imagery of the patient's anatomy taken from a first viewpoint defined by the distally-advanced imaging head; retracting the delivery sheath proximally, relative to the implant, to a partial-deployment position in which the implant is at least partially uncovered while still being retained by the delivery sheath; retracting the imaging head proximally, relative to the implant, into a retracted position in which the imaging head defines a second viewpoint that is within and surrounded by the implant; and positioning the implant at the target site guided by imagery of the implant relative to the surrounding anatomy, taken from the second viewpoint defined by the proximally-retracted imaging head.

The patient's anatomy may be imaged from the first viewpoint substantially uninterrupted by the implant or by the delivery sheath. The implant may be imaged relative to the surrounding anatomy from the second viewpoint disposed proximally relative to a distal end of the implant, substantially uninterrupted by the delivery sheath. The outer element and the imaging head may be moved together in the proximal direction.

The inventive concept also embraces a method of deploying an expandable implant within a patient's urethra. The method comprises: inserting a delivery tube into the urethra with the implant and an imaging device retained within and covered by the delivery tube; retracting the delivery tube proximally, relative to the implant, to a partially-retracted position in which the implant is at least partially uncovered while still being retained by the delivery tube; using the imaging device to image the implant together with the patients anatomy; positioning the implant at a target site within the urethra; and deploying the implant at the target site by further retracting the delivery tube to an extent sufficient to release the implant from the delivery tube.

More specifically, the delivery tube images the anatomy by a camera or other image sensor that sits within an innermost channel of the delivery system and within the inner diameter of the implant. In the partially-retracted position, the implant can be lined up with the anatomy using the camera that generates images from within the implant. After deploying the implant at the target site by further retracting the delivery tube, the camera can image the deployed device within the anatomy with no further manipulation of handle components being required by the user.

Deploying the expander in a two-stage deployment process and under direct vision from the imaging device beneficially reduces the risk of the clinician deploying the implant incorrectly. Furthermore, the partially-retracted position allows the implant to be aligned with the anatomy when it is partially uncovered and when the imaging device is located inside the implant. Imaging the expander with an imaging device located within the implant allows concentric imaging of the expander and the anatomy so that an alignment step can be completed with the anatomy and expander in the same plane aligned with a central axis, which facilitates accuracy of deployment.

Inserting the delivery tube when the implant is covered by an outer sleeve is beneficial as it allows the delivery device to be easily inserted into the urethra without the implant potentially catching on the anatomy. Advantageously, the delivery tube may have a rigid distal tip portion to manipulate and straighten the prostatic urethra, ensuring that the prostatic urethra, the surrounding anatomy and the expander implant will be substantially concentric. Optionally, the delivery tube can steer the implant in response to control inputs from its proximal end.

In one embodiment the method may comprise positioning the implant at the target site at a longitudinal position in the urethra between the patient's bladder neck and external sphincter. The method may comprise advancing a distal end of the delivery tube distally along the urethra to, or distally beyond, the bladder neck. The distal end of the delivery tube may therefore be advanced into the bladder. This allows the anatomy along the length of the urethra to be viewed as the delivery device is advanced along the urethra. This allows the clinician to check for any obstructions within the urethra and to view the prostatic lobes.

The method may then comprise pulling the distal end of the delivery tube back away from the bladder neck in a proximal direction. The bladder neck may thereby be used as a datum for positioning the implant at an appropriate longitudinal position in the prostatic urethra. The delivery tube may comprise graduation marks with which to position the implant in a clinically acceptable position relative to the bladder neck datum prior to deployment.

Positioning the expandable implant may also comprise turning or rotating the implant about a longitudinal axis of the delivery tube when positioning the implant at the target site. The implant may be rotated to align the implant with at least one prostatic lobe of the patient. For example, the implant may comprise at least one apex and may be rotated to align the at least one apex with a prostatic lobe. The implant may be secured relative to the delivery tube such that rotating the delivery tube rotates the expander. The method may comprise aligning at least one apex of the implant with the or each prostatic lobe.

The delivery tube may comprise an inner tube that is static relative to the prostatic urethra when the delivery tube is moved from the partially-deployed configuration to the fully-deployed configuration. The method may comprise holding the implant substantially stationary relative to the prostatic urethra when further retracting the delivery tube from the partially-deployed to the fully-deployed position. This is beneficial as the expandable implant may be secured to the inner tube when in the partially-deployed configuration and thus the expander may remain in a substantially unchanged longitudinal position when the delivery device is moved to the fully-deployed configuration. This improves the accuracy of deployment of the implant from a stored state to a deployed state within the prostatic urethra.

Deploying the implant may comprise expanding the implant radially. The implant may be expanded radially from a stored or compressed state to a deployed or expanded state. The implant may be deployed by moving an outer sleeve longitudinally relative to the implant. The implant may thus be unsheathed or uncovered to allow the implant to expand radially.

Moving the delivery tube to the partially-deployed configuration may comprise operating a safety catch, latch or button to enable the delivery tube to be moved or reconfigured in that way. The method may further comprise operating the safety catch again, for example moving the safety catch to a further position, to enable the delivery tube to be further retracted from the partially-retracted position.

The method may comprise retaining the implant by engagement with retaining formations that remain covered by the delivery tube in the partially-retracted position but that are exposed by said further retraction of the delivery tube to release the implant. The method may further comprise advancing the delivery tube distally to cover the retaining formations again before removing the delivery tube from the urethra. Thus, the method may comprise moving the delivery tube from the fully-deployed configuration to the storage configuration before removing the delivery tube from the urethra.

The method may comprise viewing the implant relative to the urethra from a viewpoint within the implant and disposed proximally relative to a distal end of the implant, when the delivery tube in the partially-retracted position.

The method may comprise aligning at least one apex of the implant with the patient's verumontanum. The method may comprise locating the verumontanum between laterally-spaced longitudinally extending members or struts of the implant. The method may comprise pulling back the implant proximally while avoiding contact of the apex with the verumontanum. Apices of the implant may be aligned with respective lobes of the prostate, being lateral lobes or a transition zone and a median lobe.

The method may further comprise steering the delivery tube or manipulating the anatomy by bending at least a distal portion of the delivery tube along its length.

The invention has numerous advantages. For example, the initial field of view of an imaging device need not show the stored implant upon arriving at the prostatic urethra, hence giving an unobstructed view of the anatomy. This helps a clinician to assess the anatomy and to make a judgement on positioning the implant in accordance with the length of the prostatic urethra and the height of the bladder neck height of a particular patient.

Conversely, the positioning step may allow concentric imaging of the implant and the anatomy so that an alignment step can be completed accurately and easily, ensuring that the implant and the anatomy are substantially symmetrical about the same vertical plane and have substantially the same central axis during the deployment step.

Thus, the positioning step allows a view of the implant and the anatomy at the same axial location in the anatomy. The camera lens or other image sensor and the distal tip of the expander, toward the bladder neck, are at the same longitudinal position relative to each other and can travel in this relative position, always locked together. This ensures consistent accuracy in positioning as the implant cannot move on the delivery system during introduction and positioning steps due to the retention features on the distal tip portion of the delivery system.

Arranging the lens or other image sensor within the implant facilitates correct positioning of the implant relative to each critical anatomical feature namely the bladder neck, the lobes of the prostate and the verumontanum—at the same time. Viewing of the implant and the anatomy in the same plane, not from a viewpoint behind or beside the implant, facilitates precision of alignment.

A rigid distal tip of the delivery system straightens out the prostatic urethra and ensures that the expander and the prostatic urethra, and therefore the surrounding anatomy, will be substantially concentric. Thus, the camera lens or other image sensor is oriented and located within the implant, imaging beneficially from the inside outwardly. More generally, a steerable tip allows for positioning to suit the curvature, angle or inclination of the prostatic urethra. In this respect, embodiments of the invention combine a steering ring with implant holding features in a manner that is not suggested in the prior art.

Advantageously, no balloon or other positioning device is required in the bladder, hence reducing the duration and complexity of the procedure. Nor is there a need for deployment in the bladder and pulling back, which could also damage the bladder neck.

A simple handle mechanism can effect deployment. The implant is pre-formed and there is no need to adjust or to form the implant in situ, Parts of a delivery handle lock together and control the movement and organisation of delivery sheaths and an imaging sheath. The delivery sheath has features to hold the implant in a locked position relative to the imaging component. The outer sheath moves back or is dimensioned such that it does not obscure viewing of the implant and anatomy during deployment.

The skilled reader will appreciate that whilst the expander described herein is for use in treating BPH, the delivery system of the invention could be used in other applications in which an expandable implant is to be located within a body lumen.

BRIEF DESCRIPTION OF THE DRAWINGS

Embodiments of the invention will now be described, by way of example only, with reference to the accompanying drawings, in which.

DETAILED DESCRIPTION

In general terms, embodiments of the invention relate to a delivery device for deploying an expandable implant, or expander, within the prostatic urethra of a patient to alleviate the symptoms of BPH. In a broad sense, the delivery device comprises a handle operatively connected to an elongate delivery tube. The delivery tube comprises an inner tube surrounded by an outer sleeve or sheath with an annulus defined between them. The expander may be retained in a compressed or stored configuration within the annulus. A retention feature positioned at a distal end region of the inner tube retains the expander relative to the inner tube in the compressed or stored configuration within the annulus. An imaging component is housed in or supported by the inner tube.

In use, the delivery tube is inserted into a patient's urethra through the penis and advanced along the urethra to the prostatic urethra. When satisfied that the distal end portion, and thus the expander, is accurately positioned within the prostatic urethra, the clinician operates the handle to retract the outer sheath, thereby allowing the expander to expand and deploy within the prostatic urethra.

Deployment of the expander from the delivery device may be a two-stage process in which the outer sheath is first retracted to a partially-deployed position. In the partially-deployed position, the expander is at least partially unsheathed but remains attached to the delivery device. If the clinician is satisfied that the expander is located correctly following an imaging step and an alignment step, the outer sheath may be moved to the fully-deployed position to release the expander from the delivery device, thereby locating the expander at the target site within the body lumen, in this example the prostatic urethra.

The delivery device advantageously allows the expander to be positioned accurately within the anatomy before being deployed within the prostatic urethra in a controlled manner under direct vision. Controlled deployment beneficially prevents the expander being deployed inadvertently and ensures that the expander is accurately positioned within the prostatic urethra upon and after deployment.

Figure 1:
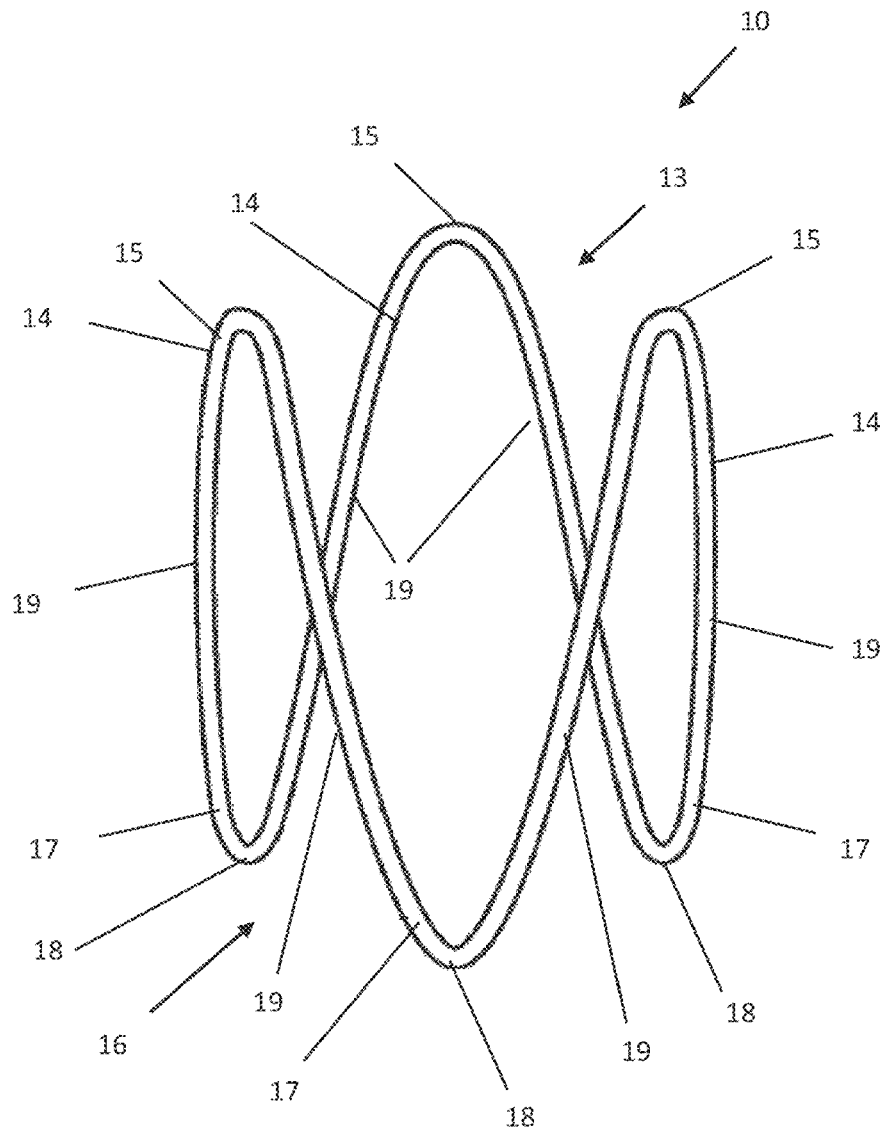
FIG. 1 is a perspective view of an expander in an expanded state suitable for use with embodiments of the invention.

To place embodiments of the invention in a suitable context, reference will firstly be made to FIG. 1 which shows a schematic diagram of an expandable implant or expander 10 suitable for use with embodiments of the present invention. The skilled reader will understand that the expander 10 shown in FIG. 1 is by way of example only and that the delivery device described herein may be suitable for use, or may be adapted for use, with other implants.

Figure 2:
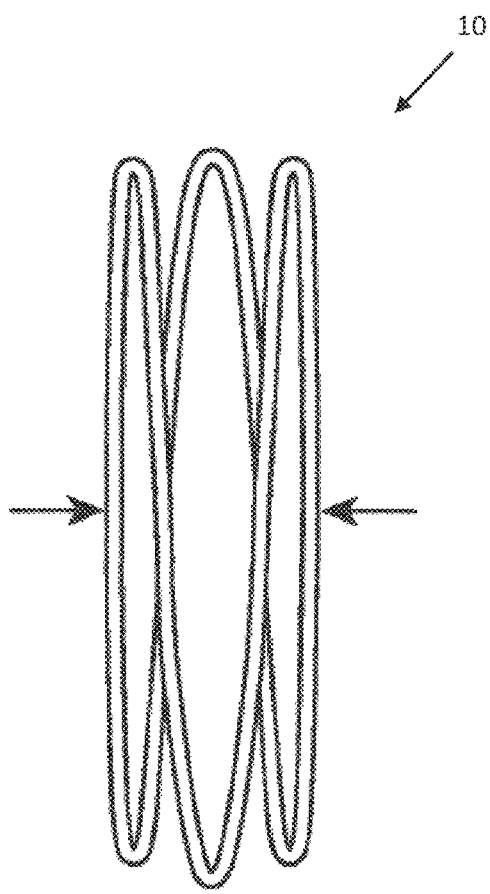
FIG. 2 is a perspective view of the expander of FIG. 1 in a stored state.

The expander 10 comprises a single nitinol wire arranged to form a sinusoidal ring. The expander 10 can be moved or transformed elastically between an expanded or deployed state as shown in FIG. 1 and a compressed or stowed state as shown in FIG. 2. When released, expander 10 will move or transform itself by elastic recovery from the compressed or stowed state of FIG. 2 into the expanded or deployed state of FIG. 1. Specifically, the nitinol wire ring of the expander 10 acts with superelastic shape memory properties such that when in the compressed state the expander 10 exerts an outward radial force urging itself to the expanded state.

The expander 10 has a proximal end 16 comprising three proximal prongs 11 with respective apices 13 and a distal end 13 comprising three distal prongs 14 with respective apices 15. The apices 15, 18 of the distal and proximal ends 13, 16 are joined, in circumferential alternation, by longitudinal struts 19.

When the expander 10 is in the contracted or compressed state shown in FIG. 2, the diameter of the sinusoidal ring defined by the expander 10 is reduced such that the expander 10 may be advanced along the urethra of a patient with minimal discomfort. The expander 10 is delivered to the prostatic urethra 30 in that contracted or delivery state.

Figure 3:
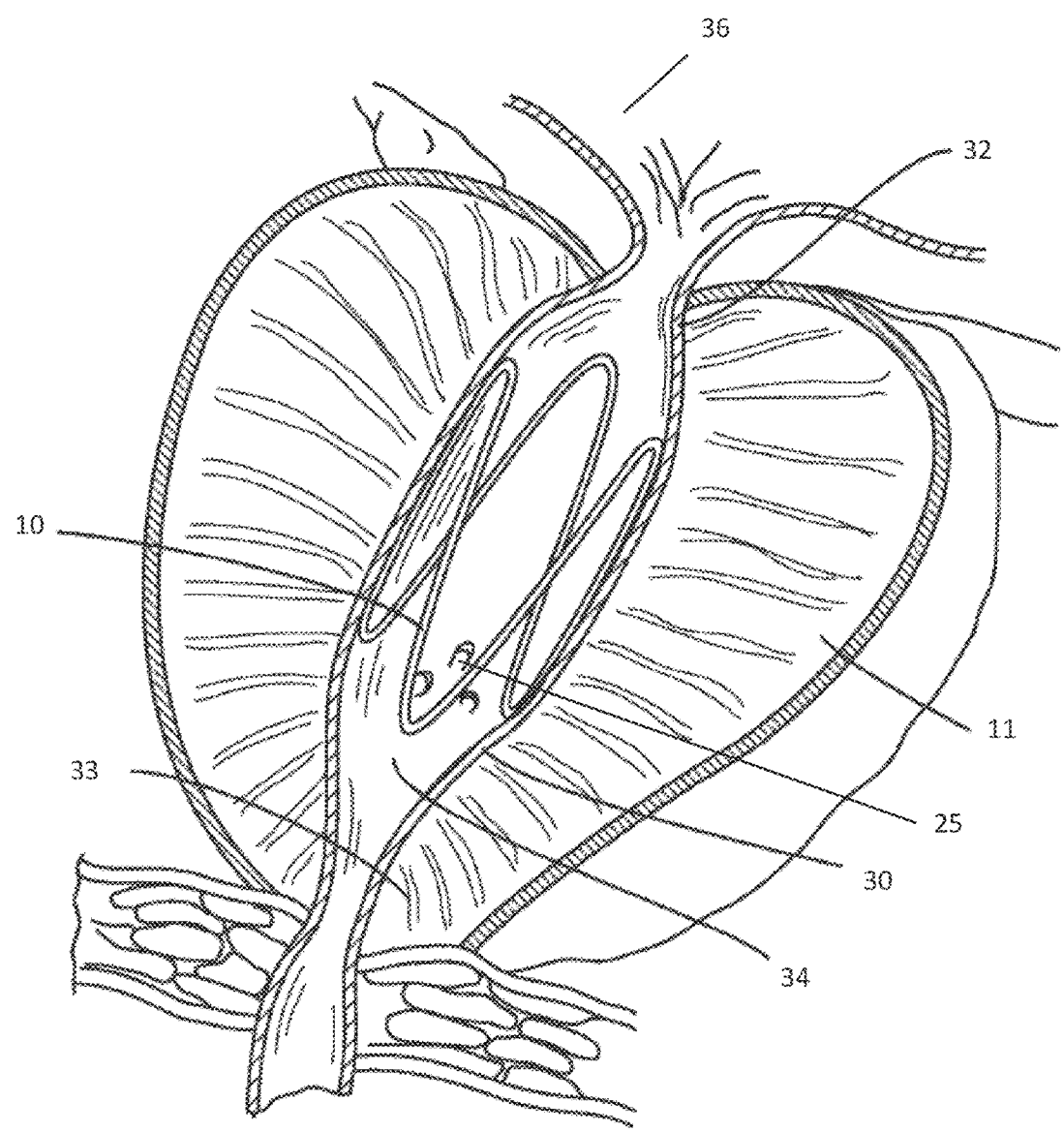
FIG. 3 is a cross-sectional view of a prostate and prostatic urethra with the expander of FIG. 1 in use for the treatment of BPH.

Referring now to FIG. 3, the expander 10 is shown in use in the treatment of benign prostatic hyperplasia (BPH) within the prostate 11. In use, the expander 10 is located within the prostatic urethra 30 between the bladder neck 32 and the external sphincter 33. When located in this position, the expander 10 exerts an outward radial force against the surrounding walls of the prostatic urethra 30 to promote the flow of urine from the bladder 36.

Positioning the expander 10 at the correct longitudinal position between the bladder neck 32 and the external sphincter 33 is challenging and care must be taken to ensure that the expander 10 is suitably positioned prior to deployment. Positioning the expander 10 too close to either the bladder neck 32 or the external sphincter 33 is undesirable as their muscle action could otherwise cause the expander 10 to migrate over time.

As shown in FIG. 3, the expander 10 is orientated angularly such that the verumontanum 25 and the seminal ducts 34 are unobstructed by the wire of the expander 10, thus preserving the patient's sexual function. Furthermore, the longitudinal struts 19 of the expander 10 are oriented to engage each respective lobe of the prostate 11, thereby exerting an outward radial force on each lobe to maintain an open passage between the bladder neck 32 and the external sphincter 33.

Figure 4:
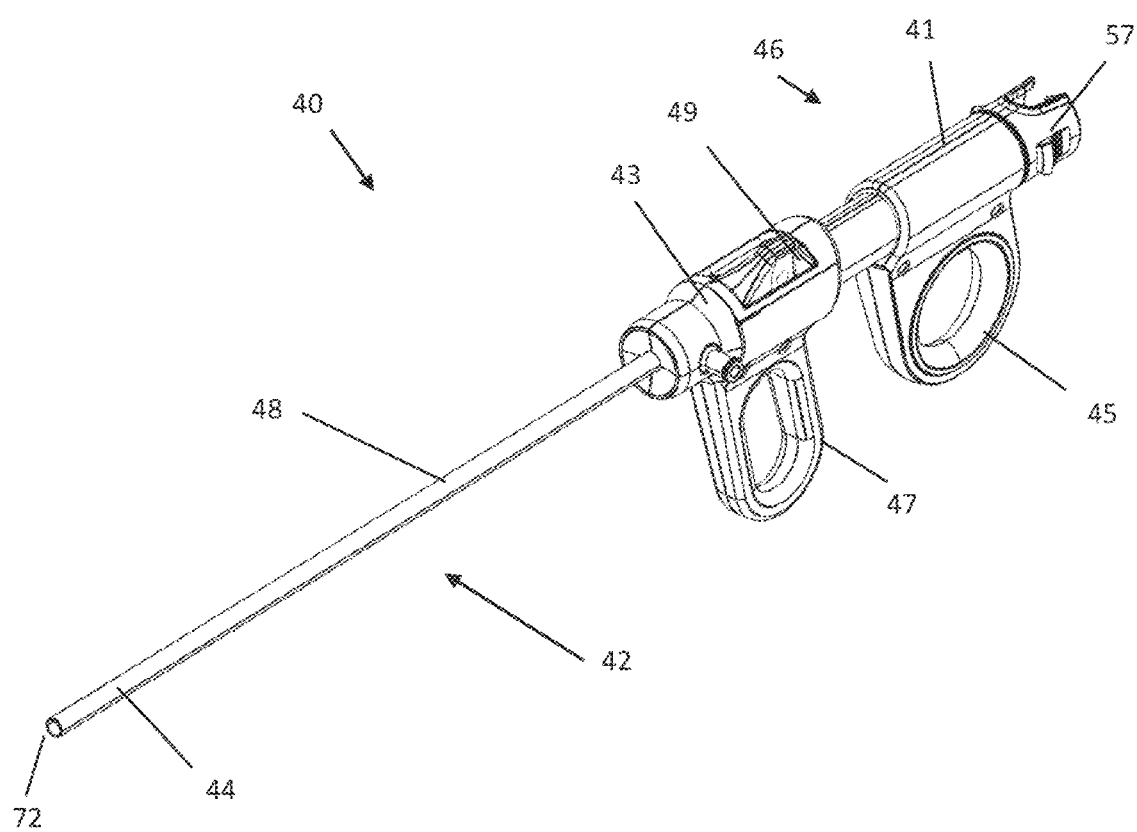
FIG. 4 is a perspective view of a delivery device according to an embodiment of the invention.

Turning now to FIG. 4, a delivery device 40 for positioning the expander 10 within the prostatic urethra 30 is shown. The delivery device 40 comprises a handle 46 operatively connected to an elongate delivery tube 42. The delivery tube 42 is configured to at least partially receive the expander 10 in a compressed state and to deploy the expander 10 within the prostatic urethra 30 of a patient. The delivery tube 42 may be inserted into the urethra via the patient's penis and advanced along the urethra to a target site, in this example the prostatic urethra 30, where the expander 10 may be deployed.

Figure 5:
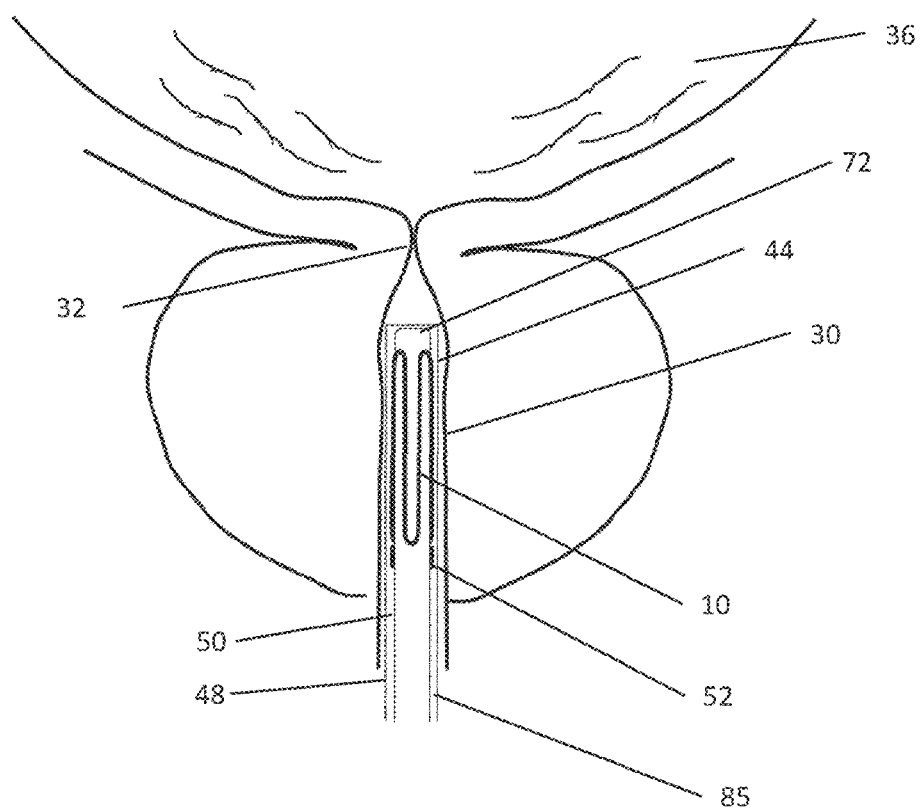
FIG. 5 is a schematic view of the distal end of the delivery device of FIG. 4 positioned within the prostatic urethra of a patient.

FIG. 5 shows a schematic view of the distal end portion 44 of the delivery tube 42 located within the prostatic urethra 30. As shown in FIG. 5, the delivery tube 42 comprises an inner tube 50 that is surrounded by an outer sleeve 48. An annulus 85 is defined between the inner tube 50 and the outer sleeve 48 and the expander 10 is located within the annulus 85. The outer sleeve 48 surrounds the expander 10 thereby preventing the expander 10 from expanding from the stored configuration to the deployed configuration. The annulus 85 serves to retain the expander 10 at the distal end region 44 of the delivery tube 42 and further acts as an irrigation channel along which fluids may be irrigated to or from the urethra and/or bladder 36.

The handle 46 is operatively coupled to the delivery tube 42 such that operating the handle 46 allows a clinician to move the outer sleeve 48 longitudinally relative to the inner tube 50. The lumen 70 on the inner tube 50 may extend through the handle 46 and terminate at a proximal end of the handle 46 in a telescope plug 57 suitable for receiving an imaging device, such as a telescope. The plug 57 may be configured to retain a telescope within the inner lumen 70 such that the telescope can provide images from the distal end 44 of the delivery tube 42. Beneficially, the plug 57 is positioned on the proximal handle 41 which is connected to the inner tube 50 and outer tube 48. As such, the telescope is fixed relative to the outer sleeve 48 and always moves with it so that the telescope also moves longitudinally relative to the inner tube 50 when the clinician operates the handle 46. The plug 57 advantageously provides a datum against which the position of the expander 10 may be measured in relation to the distal tip of the telescope and the outer sleeve 48.

The outer sleeve 48 is movable between a sheathing or storage position in which the expander 10 is surrounded by the outer sleeve 48 along its length, as shown in FIG. 5, and a deployed or retracted position in which the outer sleeve 48 is moved proximally relative to the inner tube 50 to uncover the expander 10 carried by the delivery tube 42. Furthermore, the outer sleeve 48 is movable to, and can be held temporarily at, an intermediate or partially-deployed position in which the expander 10 is partially uncovered but retained on the inner tube 50 as is described in further detail below.

The inner tube 50 comprises retention formations 52 for preventing longitudinal or angular movement of the expander 10 relative to the inner tube 50 when the expander 10 is being retained in the stored configuration within the delivery tube 42. The retention formations 52 are positioned at the proximal end 16 of the expander 10 at a longitudinal position such that the entire length of the expander 10 is retained within the outer sleeve 48 at the distal end portion 44 of the delivery tube 42 when the outer sleeve 48 is in the storage configuration. The retention formations 52 keep the expander 10 in fixed relation to the distal lens of the telescope or other distal imaging device.

FIG. 5 shows an embodiment in which the distal end portion 44 of the inner tube 50 extends along the longitudinal length of the expander 10 such that the expander 10 is supported along substantially its entire length by the inner tube 50. Supporting the expander 10 along its full length is beneficial when the expander 10 is being advanced along the urethra as it prevents the expander 10 deforming and potentially disengaging the retention formations 52. However, in another embodiment, the distal tip 72 of the inner tube 50 may extend distally from the retention formations 52 only part-way along the length of the expander 10.

Figure 6:
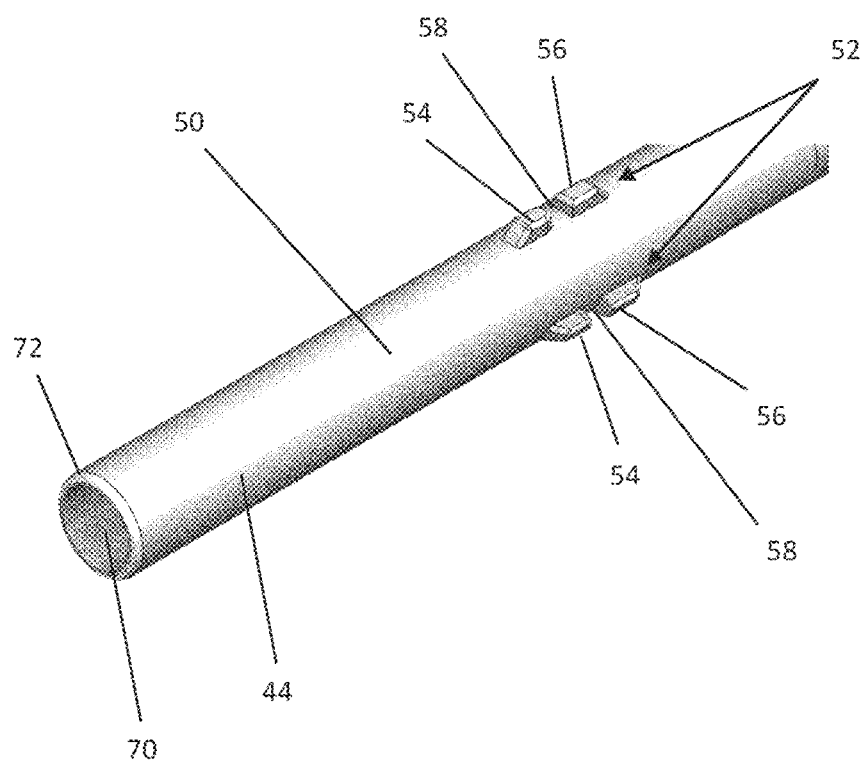
FIG. 6 is a perspective view of an underside of the distal end of the inner tube of the delivery device of FIG. 4.

Turning now to FIG. 6, a perspective view of the underside of the distal end portion 44 of the inner tube 50 is shown with the outer sleeve 50 and imaging device removed for clarity. The inner tube 50 is an elongate plastics tube comprising the distal end portion 44 opposed to a proximal end coupled to the handle 46. The inner tube 50 comprises a hollow inner lumen 70 that may be used to receive the imaging device, for example the telescope or an imaging chip with a related support and electronics.

Figure 7:
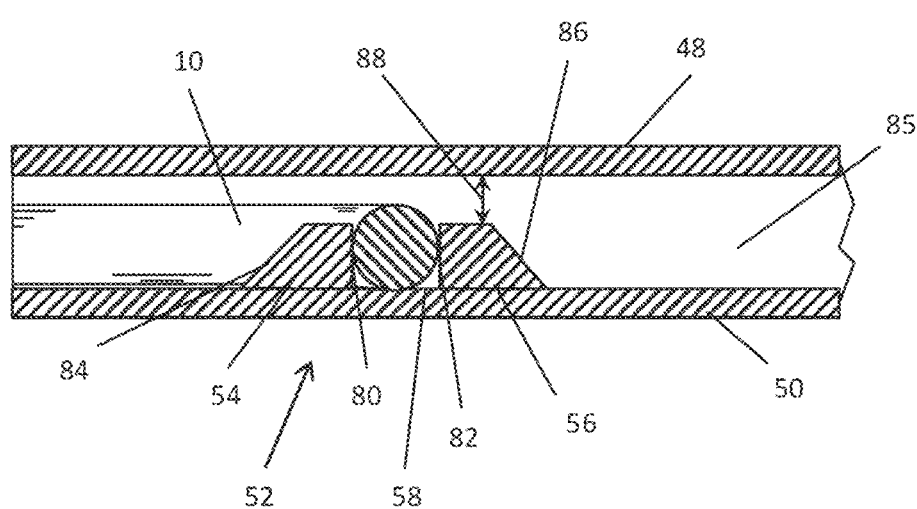
FIG. 7 is a longitudinal sectional view of a retention formation and expander on the inner tube of FIG. 6.
Figure 8:
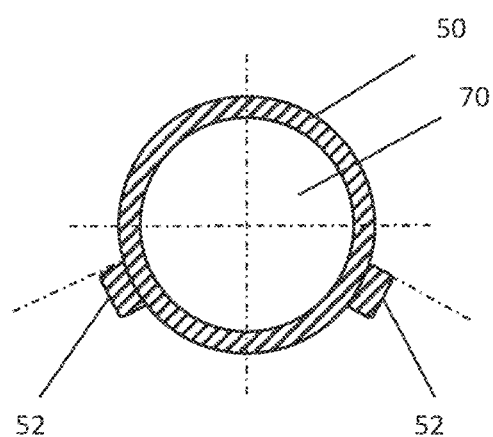
FIG. 8 is a cross-sectional view of the distal end of the inner tube of FIG. 6.

As shown in FIGS. 6 to 8, the inner tube 50 comprises two sets of retention formations 52. The retention formations 52 are configured to prevent longitudinal or rotational movement of the expander 10 relative to the inner tube 50 and to prevent rotational movement of the expander 10 relative to the telescope. The retention formations 52 are located on the distal end portion 44 of the inner tube 50.

Typically, the retention formations 52 are positioned on the inner tube 50 at a position proximal of the distal tip 72 by a distance in excess of the length of the expander 10. This is beneficial as when the expander 10 is in the stored position, the inner tube 50 may provide an orifice or aperture for a telescope to visualise the anatomy, with or without the expander also being visible, and can support the expander 10 along the entire length of the expander 10. This maintains the longitudinal struts 19 generally parallel to each other when in the stored position, thus promoting smooth deployment of the expander 10 from the stored position to the expanded position.

Alternatively, when the inner tube 50 is shorter than the outer sleeve 48 such that the outer sleeve 48 overhangs the inner tube 50, the retention formations 52 may be located such that the distal end 13 of the expander 10 also overhangs the distal end of the inner tube 50, in this embodiment, the inner tube 50 only provides support to a portion of the expander 10. However, the support provided by the inner tube 50 is again sufficient to maintain the longitudinal struts 19 generally parallel to each other when the expander 10 is in the stored configuration.

The retention formations 52 each comprise a distal protrusion 54 and a proximal protrusion 56 that define a retention slot 58 between them. The slot 58 is configured to receive a proximal apex 18 of the expander 10 so as to retain the expander 10 on the inner tube 50. When the expander 10 is located on the inner tube 50 in the compressed configuration, the proximal prong 17 of the expander 10 wraps around and engages the distal protrusion 54 of the retention formation 52. This inhibits longitudinal movement of the expander 10 in the distal direction and also rotational movement of the expander 10 relative to the inner tube 50. The proximal apex 18 may also abut the proximal protrusion 56, thereby inhibiting movement of the expander 10 longitudinally in the proximal direction.

FIG. 7 is a longitudinal sectional view of a retention formation 52 with the expander 10 in the stored configuration and surrounded by the outer sleeve 48. The retention formation 52 prevents longitudinal or rotational movement of the expander 10 relative to the inner tube 50. As shown in FIG. 7, the outer sleeve 48 of the delivery device 40 surrounds the expander 10 thereby preventing radially-outward expansion of the expander 10 to the deployed position. FIG. 7 shows the outer sleeve 48 in a storage or partially-deployed position in which the expander 10 is encircled by the outer sleeve 48 at least in alignment with the retention formations 52, thereby retaining the expander 10 in the stored configuration on the inner tube 50.

The distal protrusion 54 and a proximal protrusion 56 of the retention feature 52 are shown in detail in FIG. 7. The protrusions 54, 56 each comprise a ramped wall 84, 86 such that the retention feature 52 has ramped walls 84, 86 on the distal and proximal sides of the retention feature 52.

The ramped walls 84, 86 of the protrusions 54, 56 minimise the potential for the retention features 52 to re-engage or catch on the expander 10 after the expander 10 has been deployed within the prostatic urethra 30. The ramped walls 84, 86 are opposed about the retention slot 58 of the retention feature 52. Thus, if the inner tube 50 is moved longitudinally relative to the deployed expander 10 when the outer sleeve 48 is in the deployed position, the ramped surfaces 84, 86 may contact the expander 10 but are unlikely to catch or snag on the expander 10. This is advantageous as catching or snagging the expander 10 once it is deployed could cause the expander 10 to move longitudinally within the anatomy, which could result in the expander 10 being positioned incorrectly.

Furthermore, the proximal protrusion 56 and distal protrusion 54 comprise generally vertical walls 80, 82 that define the sides of the slot 58 such that the slot 58 has a U-shaped profile. The vertical walls 80, 82 of the protrusions 54, 56 advantageously act as a guide to radial expansion of the expander 10 when the expander 10 is being deployed. Specifically, the walls 80, 82 confine expansion movement of the expander 10 to a substantially radial direction when the expander 10 is being deployed, thereby minimising unintended longitudinal movement of the expander 10 relative to the inner tube 50 during deployment.

The slot 58 defined by the distal protrusion 54 and the proximal protrusion 56 may be dimensioned to have a clearance fit with the wire of the expander 10. In another embodiment, the slot 58 may have an interference fit with the wire of the expander 10 such that the slot 58 applies a retaining force on the expander 10. However, the retaining force applied by the slot 58 should be less than the radially-outward self-expansion force of the expander 10 such that the expander 10 may still be deployed when the outer sleeve 48 is pulled back to the deployed position.

As shown in FIG. 7, a gap 88 is provided in the annulus 85 between the top or radially-outer surfaces of the protrusions 54, 56 and the inner surface of the outer sleeve 48. The width of the gap 88 is less than the diameter of the wire of the expander 10 such that the expander 10 is retained within the slot 58 when the outer sleeve 48 is in the storage position. The expander 10 may contact the inner surface of the outer sleeve 48 when the expander 10 is being retained in the stored position by the outer sleeve 48 and retention formations 52.

FIG. 8 is a cross-sectional view of the inner tube 50 and the retention formations 52. As shown in FIG. 8, the inner tube 50 comprises two retention formations 52 for retaining the expander 10 on the inner tube 50. The retention formations 52 are spaced apart from each other angularly by about 120° such that the retention formations 52 may engage two of the proximal prongs 17 of the expander 10, More generally, with reference to the circumference of the inner tube 50, the retention formations 52 are at approximately the four to five o'clock and seven to eight o'clock positions respectively.

It will be noted that, in this example, the retention formations are on the underside of the inner tube 50, in substantially symmetrical positions about a central longitudinal plane of the inner tube 50, but that no retention formation 52 is provided on top of the inner tube 50. This is in case the anterior prostatic urethra contacts and presses on the upper surface of the inner tube 50 during deployment of the expander 10, in which case such pressure could prevent the expander 10 disengaging from a retention formation 52 positioned on top of the inner tube 50. However, this configuration of the retention formations 52 is not essential. Where there is less concern as to reliable deployment, retention features could be positioned anywhere on the inner tube 50, including its top; for example, three substantially equi-spaced retention features would be possible.

The skilled reader will understand that the retention formations 52 may be spaced angularly by any angle that is suitable for engaging and retaining an expander on the inner tube 50. Furthermore, the skilled reader will understand that the inner tube 50 may comprise more or fewer than two retention formations 52 to engage and retain the expander 10.

The retention formations 52 are positioned angularly on the inner tube 50 such that when the delivery tube 42 is inserted into the urethra with the handle 46 in an ergonomic, generally upright position, the expander 10 is already oriented to engage the lobes of the prostate 11. This is beneficial as the clinician is only required to make small adjustments, if any, to the angular position of the expander 10 when positioning the expander 10 within the prostatic urethra 30.

Figure 9:
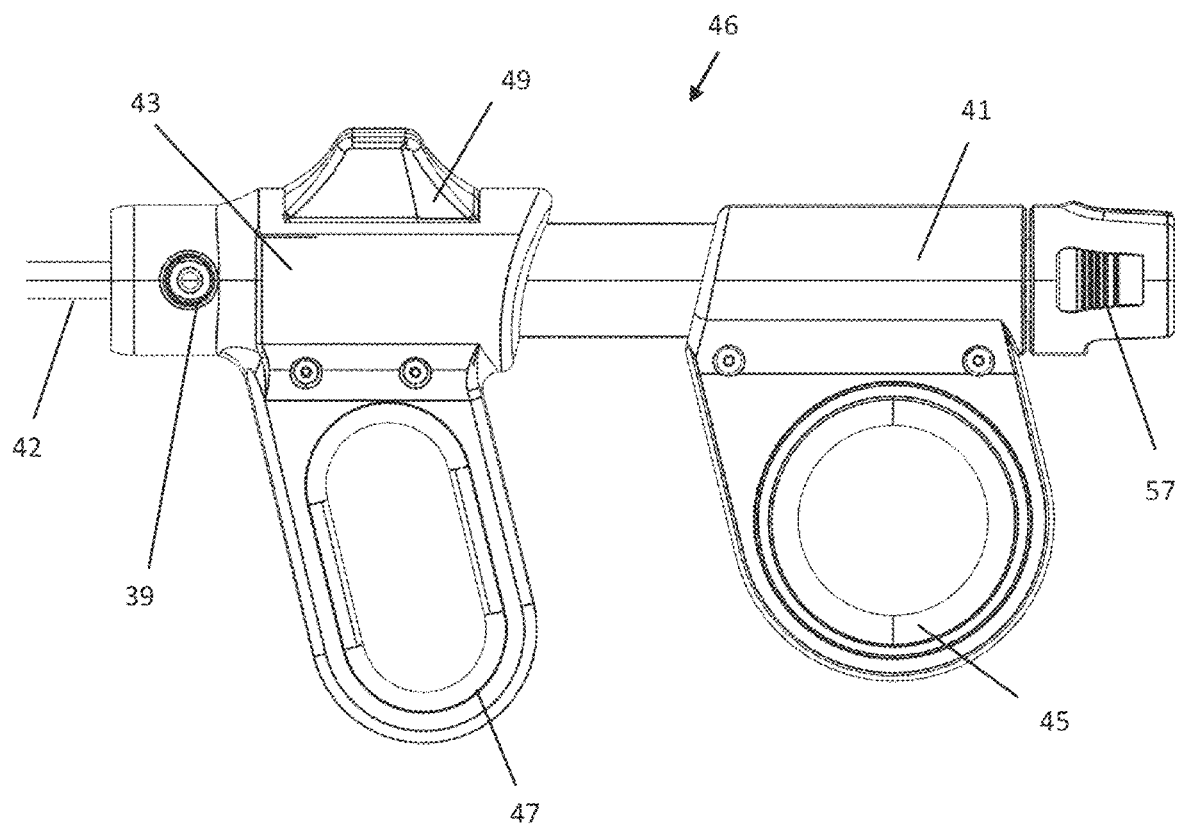
FIG. 9 is a schematic side view of a handle of the delivery device of FIG. 4.

FIG. 9 is a side view of the handle 46 of the delivery device 40. The handle 46 is connected to the proximal end of the delivery tube 42 such that the handle 46 may be held by a clinician and used to position the delivery tube 42. Furthermore, the handle 46 is operable to control the position of the cuter sleeve 48 relative to the inner tube 50 such that the outer sleeve 48 may be moved between the storage position, the partially-deployed position and the fully-deployed position thereby allowing a clinician to deploy the expander 10 by operating the handle 46. The handle 46 is also operable to control the position of the imaging sheath relative to the inner tube 50 and the outer tube 48.

The handle 46 further comprises an irrigation duct 39 that is fluidly connected to the annulus 85 of the delivery tube 42. An irrigation reservoir may be coupled to the irrigation duct 39 such that fluid may be circulated via the annulus 85 to clear the field of view of the imaging device 90 if debris or blood obscures or blocks the field of view of the imaging device. The irrigation duct 39 can also be connected to a vacuum such that the annulus 85 can be used to drain fluid from the bladder 36 and/or urethra to a waste reservoir, not shown.

The handle 46 is designed to be operable by the clinician using one hand. Specifically, the handle 46 comprises a proximal grip 41 and a distal grip 43 that are movable longitudinally relative to each other. Moving the proximal grip 41 relative to the distal grip 43 causes the outer sleeve 48 and telescope to move longitudinally relative to the inner tube 50. For this purpose, the proximal grip 41 may be connected to the inner tube 50 and the distal grip 43 may be connected to the outer sleeve 48 and telescope through the plug 57. As such, moving the grips 41, 43 relative to each other effects relative movement between the inner tube 50 and the outer sleeve 48 and telescope plug 57.

In this example, the proximal grip 41 comprises a thumb ring 45 into which the clinician may place a thumb and the distal grip 43 comprises a finger loop 47 into which the clinician may place their fingers. The finger loop 47 allows the clinician to pull the distal grip 43 toward the proximal grip 41 thereby moving the outer sleeve 48 and the telescope plug 57 proximally relative to the inner tube 50. This is beneficial as it ensures that the inner tube 50 and thus the expander 50 is held static with respect to the prostatic urethra 30 during deployment and allows the telescope and outer sleeve 48 to move together. Also advantageously, the clinician can view and confirm that the apices of the expander 10 are positioned correctly relative to the anatomy and therefore can deploy the expander 10 in the desired location within the anatomy.

Furthermore, the clinician may operate the proximal and distal grip in reverse, for example by pushing their fingers against the distal side of the finger loop 47, opening the hand span and in turn moving the distal grip 43 distally relative to the proximal grip 41. This is beneficial as it allows the clinician to return the outer sleeve 48 from the fully-deployed or partially-deployed position to the storage position.

The handle 46 further comprises a safety catch or lever 49 that may, for example, be located on an upper surface of the distal grip 43 or on either side of the distal grip 43 or a power grip. The lever 49 is operable to prevent or to permit movement of the proximal grip 41 and distal grip 43 relative to each other longitudinally. The lever 49 may, for example, be movable between three distinct detent positions that correspond to the storage, partially-deployed and fully-deployed positions of the outer sleeve 48.

Figure 10:
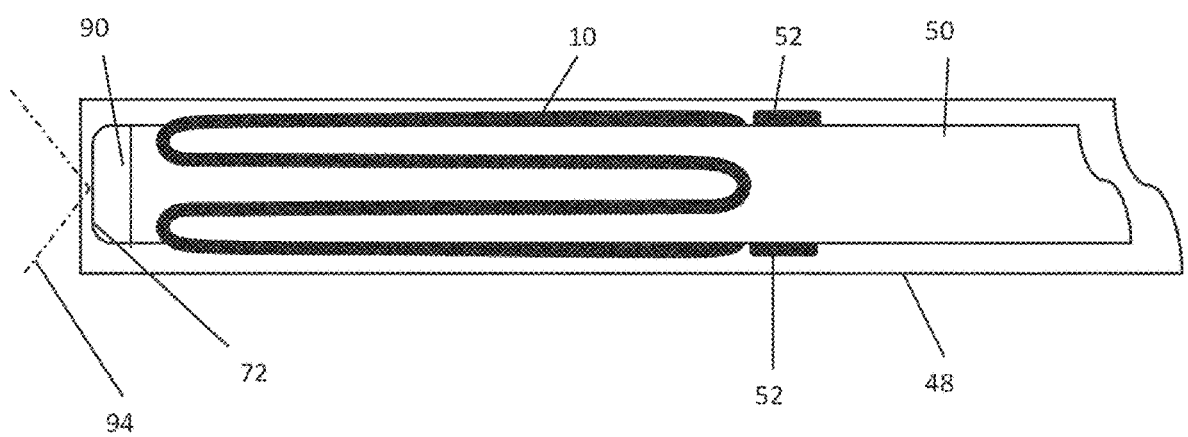
FIG. 10 is a schematic side view of the distal end region of the delivery tube and expander in a stored configuration.

For example, when the lever 49 is in the first, storage, position the proximal grip 41 and distal grip 43 are locked longitudinally relative to each other such that the outer sleeve 48 is retained in the storage position as shown in FIG. 10. This is beneficial as the clinician may insert the delivery tube 42 into the urethra via the penis without a risk of the outer sleeve 48 moving to the deployed position and causing the expander 10 to be deployed in the incorrect position.

When the distal end region 44 of the delivery tube 42 has been advanced sufficiently along the urethra, for example to the bladder neck 32 or prostatic urethra 30, the clinician may move the lever 49 to the partially-deployed position. This unlocks the proximal and distal grips 41, 43 so that the clinician may pull the proximal grip 41 back relative to the distal grip 43 to move the grips 41, 43 and hence the outer sleeve 48 of the delivery tube 42 to the partially-deployed position. At this stage, movement of the proximal grip 41 is related to the delivery tube 42 such that only a partial length of about 10 to 15 mm of the expander 10 is uncovered so that the expander 10 will not accidentally release and deploy.

Figure 11:
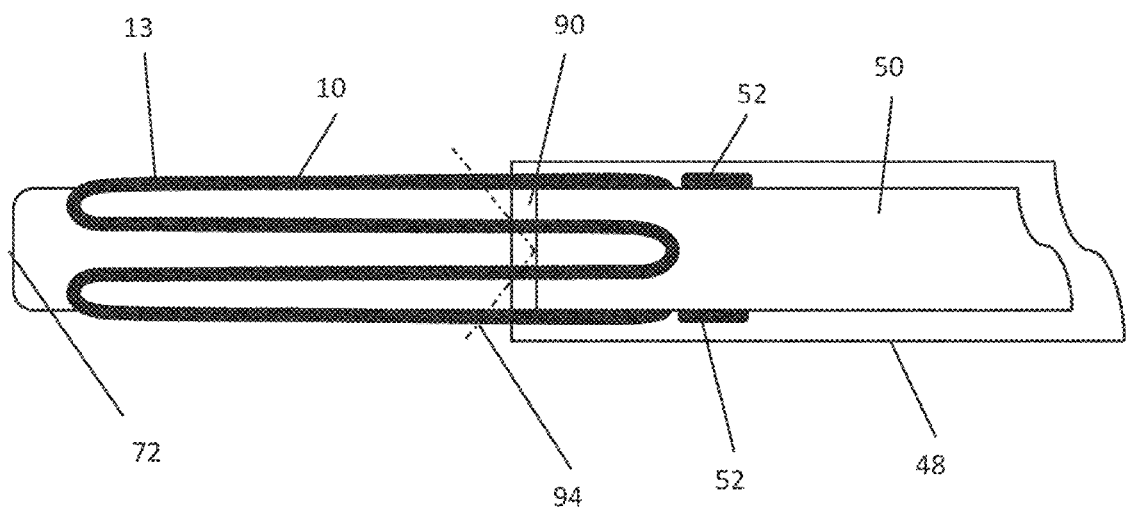
FIG. 11 is a schematic side view of the distal end region of the delivery tube and expander in a partially deployed configuration.

FIG. 11 shows a schematic plan view of the distal end region 44 of the delivery tube 42 in the partially-deployed position in which the outer sleeve 48 has been retracted to partially unsheath the expander 10. When in the partially-deployed position, the distal end of the outer sleeve 48 is positioned distally with respect to the retention formations 52 but proximally with respect to the distal end 13 of the expander 10. As such, the expander 10 is partially unsheathed but is still retained on the inner tube 50. From this position, the clinician may operate the handle 46 to return the outer sleeve 48 to the storage position if it is decided not to complete deployment of the expander 10.

Moving the outer sleeve 48 to the partially-deployed position causes the telescope 90 to move proximally such that the distal end 13 of the expander 10 comes within the field of view 94 of the telescope 90. It will be apparent that imaging takes place from the inside out, that is, from a viewpoint within the expander 10 looking out at the anatomy through at least a distal portion of the expander 10. This effectively juxtaposes the expander 10 with the anatomy and therefore provides a reliable reference for the clinician to see and appreciate the angular and longitudinal position of all parts of the expander 10 relative to the prostatic urethra 30.

Figure 12:
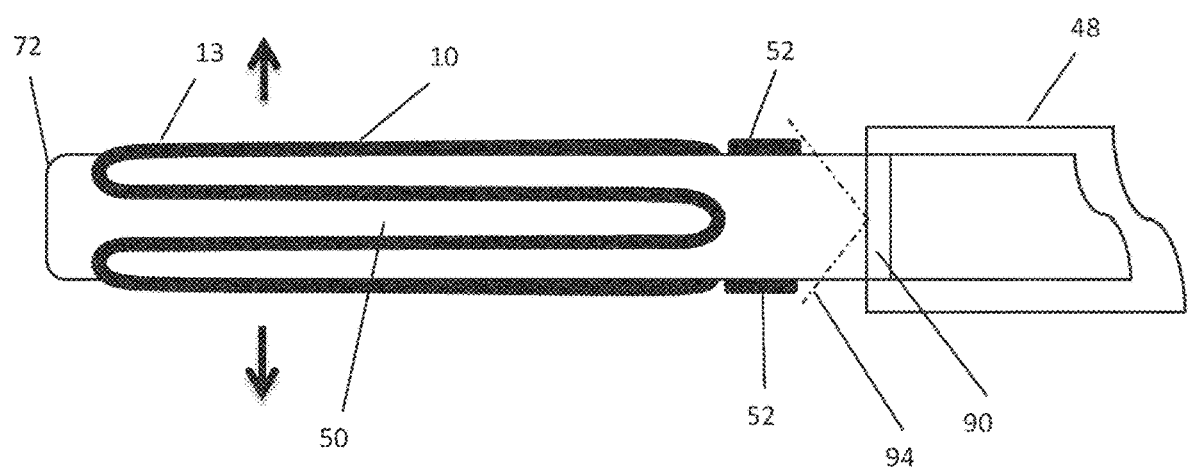
FIG. 12 is a schematic side view of the distal end region of the delivery tube and expander in a fully deployed configuration.

Once the clinician is satisfied that the expander 10 is located correctly within the prostatic urethra 30, the lever 49 is moved from its partially-deployed position to its fully-deployed position such that the distal grip 43 may be moved longitudinally towards the proximal grip 41 to its fully-deployed position. This moves the outer sleeve 48 and the telescope 90 proximally relative to the inner tube 50 as shown in FIG. 12 in which the expander 10 and retention formations 52 are fully uncovered by the outer sleeve 48. Uncovering the retention formations 52 allows the expander 10 to disengage the retention formations 52 and to expand radially to the deployed position.

The three stages of deployment, namely stowed, partially-deployed and fully-deployed, beneficially allow the clinician to deploy the expander 10 in a controlled manner and mitigates the potential for the expander 10 to be deployed accidentally or in the wrong location. For example, the lever 49 prevents accidental operation of the handle 46 that could cause the expander 10 to be deployed incorrectly. Furthermore, the inner tube 50 may be held static relative to the anatomy during operation of the handle 46 as the telescope 90 moves inside it, allowing the anatomy to be visualised together with the expander 10. This improves the accuracy of deployment of the expander 10 and promotes radial expansion of the expander 10 during deployment with minimal longitudinal movement relative to the anatomy.

Figure 13:
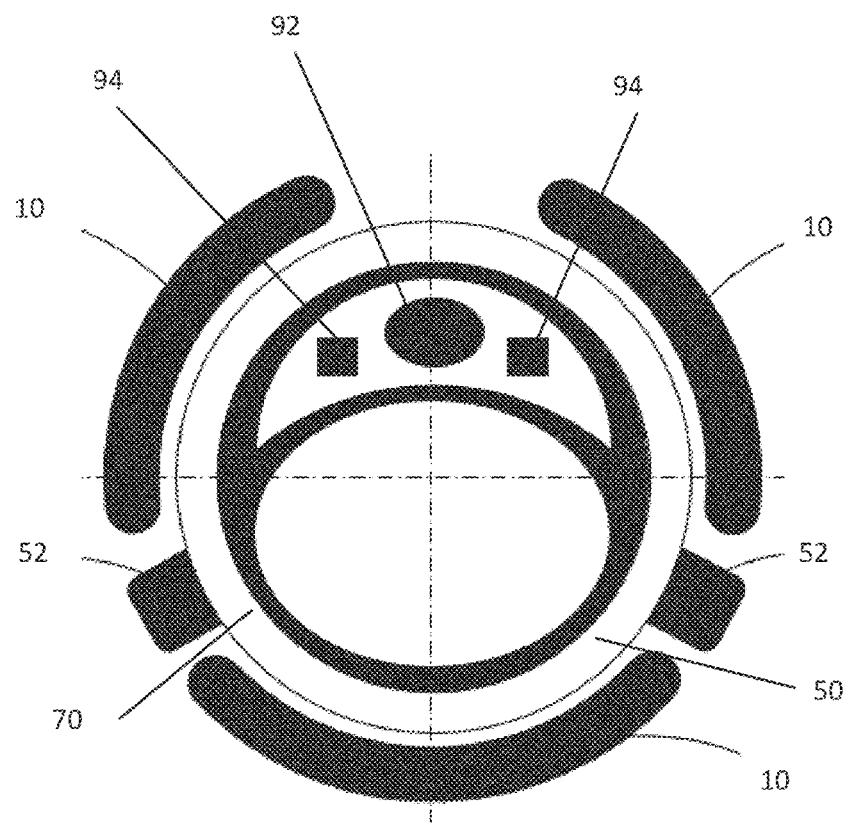
FIG. 13 is a schematic end view of the delivery device comprising an imaging device.

FIG. 13 shows an end-on view of the inner tube 50 and expander 10 in a stored configuration, with the outer sleeve 48 removed for clarity. The inner tube 50 comprises an imaging device 90 such as a telescope or imaging chip located within the inner lumen 70. The imaging device 90 shown comprises an electronic imaging chip 92, such as a CMOS chip and at least one light source 94 for illuminating the region that is being imaged by the imaging device 90. The light source 94 may be, for example, an LED or optical fibre that is configured to illuminate the area to be imaged by the imaging device 90.

The imaging chip 92 has a wide field of view, for example 120° or more, such that the clinician may view a large area of the anatomy. As shown in FIGS. 10 to 12, the field of view 94 of the imaging device 90 extends through the expander 10 when the outer sleeve 48 is in the storage configuration and the expander 10 is retained on the distal end 44 portion of the inner tube 50. This is advantageous as it allows the clinician to view the expander 10 relative to the anatomy which assists the clinician when positioning the expander 10 angularly and longitudinally within the prostatic urethra 30.

As shown in FIG. 10, when the outer sleeve 48 is in the storage position, the field of view 94 of the imaging device 90 extends through the outer sleeve 48. However, in FIG. 11 when in the partially-deployed position, the outer sleeve 48 is retracted such that it is no longer in the field of view 94 of the imaging device 90. Retracting the outer sleeve 48 out of the field of view of the imaging device 90 in the partially-deployed position is beneficial as it improves the extent and clarity of the image provided to the clinician. Furthermore, the partially-deployed position allows the distal prongs 14 of the expander 10 to contact the lobes of the prostate 11 such that the clinician may view and fully appreciate the position of the expander 10 relative the prostatic urethra 30 prior to full deployment. This advantageously enables the clinician to check if the expander 10 is positioned correctly prior to full deployment.

Figure 14:
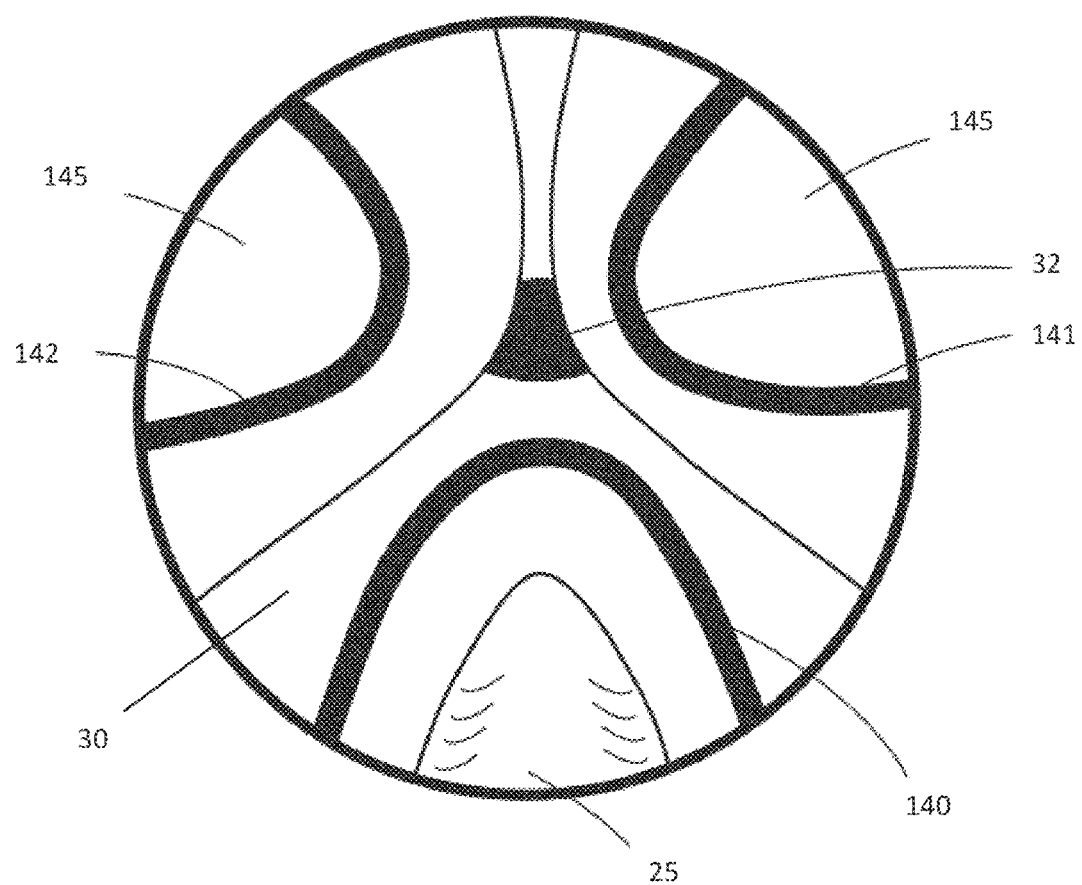
FIG. 14 is a schematic view of an image captured by the imaging device of FIG. 13.

To illustrate this, FIG. 14 is a schematic view of an image captured by the imaging device 90 when the outer sleeve 48 is in the partially-deployed position. The image of FIG. 14 shows each of the distal prongs of the expander 10 aligned with and contacting the lateral prostatic lobes around the prostatic urethra 30. Specifically, the posterior prong 140 of the expander is shown surrounding or straddling the verumontanum 25 whereas the two anterior prongs 141, 142 of the expander 10 are oriented such that they engage the anterior lobes 145.

It will be apparent that the image provided to the clinician by the imaging device 90 beneficially allows simultaneous visualisation of the longitudinal position of the expander 10 relative to the anatomy, for example the verumontanum 25 and the bladder neck 32, and also the angular position of the expander 10 relative to the verumontanum 25 and the prostatic lobes. This facilitates accurate positioning of the expander 10 within the prostatic urethra 30.

Figure 15:
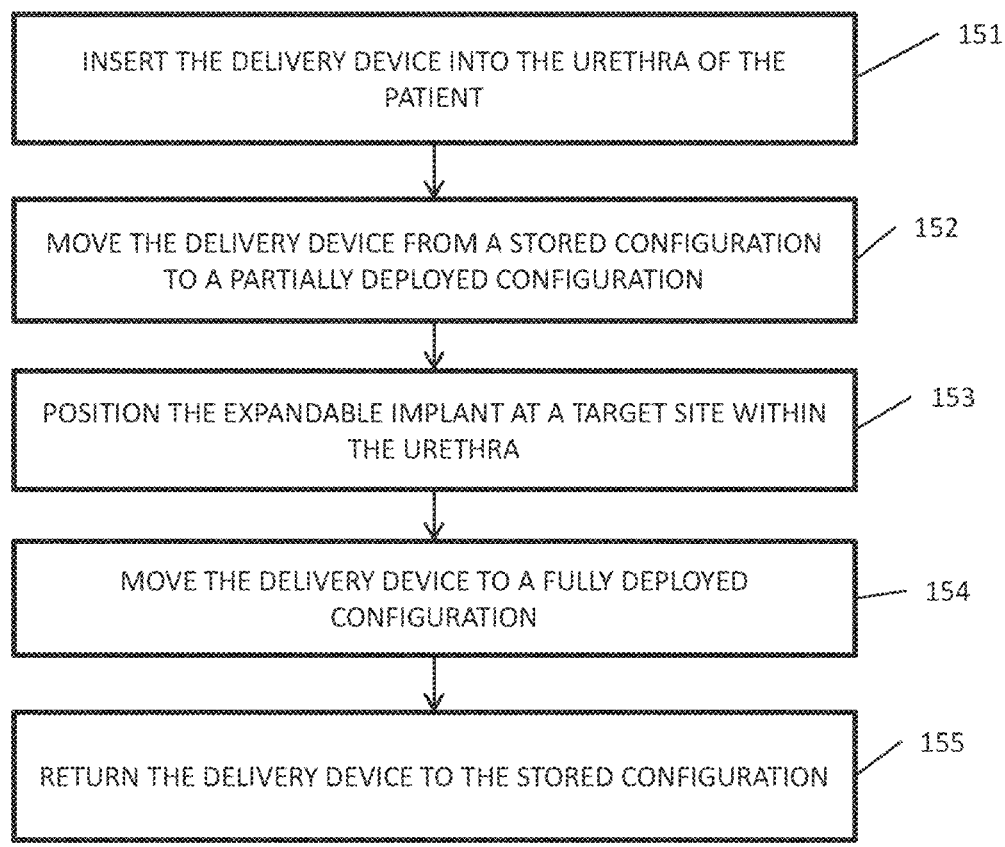
FIG. 15 is a flow chart outlining the steps of deploying an expandable implant using the delivery device of FIG. 4.

Turning now to FIG. 15, a flow chart outlining a method of deploying the expander 10 within the prostatic urethra 30 is shown. In the first step 151, the clinician inserts the delivery tube 42 of the delivery device 40 into the urethra of the patient via the penis. The delivery tube 42 is inserted into the urethra in the storage configuration such that the expander 10 is covered by the outer sleeve 48.

The delivery tube 42 is advanced along the urethra until the distal end of the delivery tube 42 reaches the bladder neck 32. As the delivery tube 42 is advanced along the urethra, the clinician may view the anatomical landmarks of the patient, for example the external sphincter 33, the verumontanum 25 and the bladder neck 32, from the image captured by the imaging device 90. This is beneficial as it allows the clinician to assess the patient and to check for any structures that may prevent the expander 10 being deployed, for example for an obstructing intravesical median lobe.

Next, in Step 152, the clinician reconfigures the delivery device 40 from the storage configuration to the partially-deployed configuration. To do so, the clinician moves the lever 49 from the stored position to the partially-deployed position and then moves the distal grip 43 in a proximal direction to move the outer sleeve 48 proximally relative to the expander 10 and the inner tube 50 such that the expander 10 is partially uncovered. This is allows the clinician to view the distal prongs of the expander 10 relative to the lateral prostatic lobes around the prostatic urethra 30.

In Step 153, the clinician positions the expander 10 at a target site in the prostatic urethra 30 by moving the distal end region 44 of the delivery tube 42 in a proximal direction from the bladder neck 32. As noted with reference to FIG. 16, the extent of proximal movement may be judged with the aid of graduation marks on the delivery tube 42 to indicate the axial distance travelled from the bladder neck 32. In this way, the bladder neck 32 may be used as a datum for positioning the expander 10 longitudinally within the prostatic urethra 30.

When the clinician is satisfied that the distal end region 44 and thus the expander 10 are at the correct longitudinal position, the clinician may then rotate the delivery device 40 to orient the expander 10 at an appropriate angle within the target site. The expander 10 is oriented such that the distal apices 15 of the expander 10 that are visible in the image captured by the imaging device 90 are aligned with the prostatic lobes around the prostatic urethra 30. The clinician may also move the delivery tube 42 in a further distal direction when the expander 10 is in the correct orientation such that the verumontanum 25 comes into view 10. The expander 10 can thereby be placed in a clinically-acceptable position between the bladder neck 32 and verumontanum 25, with the apices circumferentially targeting the lateral lobes.

If the clinician is satisfied that the expander 10 is correctly positioned within the prostatic urethra 30 then they may reconfigure the delivery device 40 to the fully-deployed configuration in Step 154. Alternatively, if the clinician is not satisfied with the position of the expander 10, the delivery device 40 may be returned to the storage configuration and the procedure may be aborted or tried again.

The delivery device 40 is moved into the fully-deployed configuration by first moving the lever 49 to the fully-deployed position before moving the distal grip 43 in a proximal direction. This moves the outer sleeve 48 and telescope proximally while keeping the inner tube 50 and thus the expander 10 static relative to the target site. In a further embodiment, the inner tube 50 may be or comprise a camera lumen that moves in the proximal direction while the expander 10 is held stationary relative to the target site. This ensures that the expander 10 is deployed in the intended position.

When the outer sleeve 48 is moved to the fully-deployed position, the proximal apices 18 disengage from the retention features 52 and expand in an outward radial direction. The walls 80, 82 of the slot 58 promote radial expansion of the expander 10 and minimise longitudinal movement of the expander 10 during deployment.

After the expander 10 has been deployed, the delivery device 40 may be returned to the storage or partially-deployed configuration in Step 155. This is beneficial as the outer sleeve 48 then covers the retention formations 52 to reduce the risk of the retention formations 52 inadvertently re-engaging and moving the expander 10 after deployment. The clinician may then view the deployed expander 10 through the imaging device 90 to check that the expander 10 is correctly positioned. Men the clinician is satisfied that the expander 10 has been deployed correctly the delivery device 40 may be withdrawn proximally from the urethra.

Figure 16:
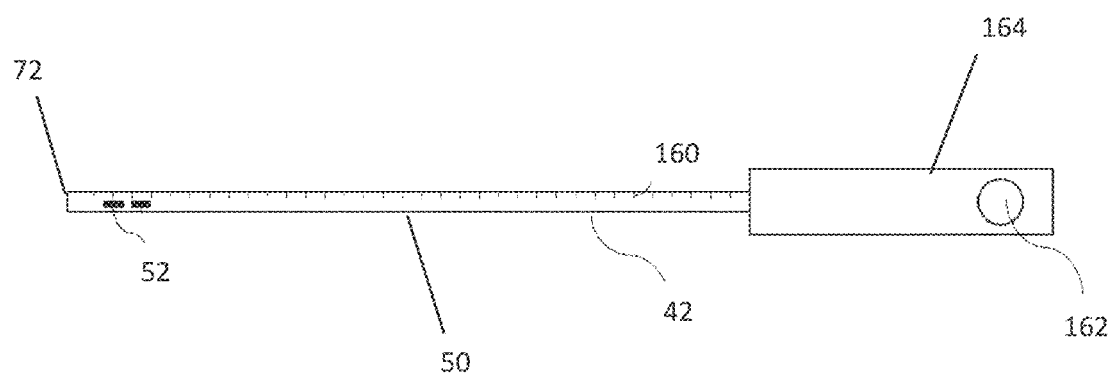
FIG. 16 is a schematic view of a tube of a delivery device according to another embodiment.

Turning now to FIG. 16, an embodiment of the delivery device 40 is shown in which the delivery tube 42 comprises a series of graduation marks 160 spaced at known intervals along the length of the delivery tube 42 to allow positioning of the expander 10, that is in a fixed position to the delivery tube 42 with the bladder neck 32. FIG. 16 shows a schematic of the inner tube 42 comprising an overmoulded hub 164 attached to a proximal end of the inner tube 50. The hub 164 comprises a boss hole 162 for attaching the hub 164 to the handle 46. The boss hole feature 162 ensures that the position of the inner tube 42 relative to the proximal grip 41 is maintained.

The graduation marks 160 are shown on the inner tube 50. However, the graduation marks 160 may be on the inner tube 50 or on the outer sleeve 48. The graduation marks 160 are visible to the clinician as the delivery tube 42 is advanced along the urethra thereby giving the clinician an indication of the longitudinal position of the distal tip 72 of the inner tube 50 within the urethra.

The skilled reader will understand that the graduation marks 160 may be positioned at any known interval suitable for positioning the delivery tube 42 longitudinally within the urethra. Furthermore, the graduation marks 160 may be numbered. The graduation marks can also be used to approximate the prostatic urethral length during the procedure, which may guide the clinician to select the most clinically acceptable position for the expander 10.

The graduation marks 160 may be used when the distal tip 72 of the inner tube 50 is located at the bladder neck 32 before moving the delivery tube 42 in a proximal direction. This is beneficial as the clinician may know that, for example, the expander 10 should be located two graduation marks proximally from the bladder neck 32. In this instance, when the proximal tip of the delivery tube 42 is located at the bladder neck 32, the clinician may then retract the delivery tube 42 by two graduation marks 160 to position the expander 10 at the desired longitudinal position. The clinician can read the graduation marks along the portion of the delivery tube 42 within the patient or outside the patient.

A delivery device 40 according to a further embodiment is described below with reference to FIGS. 17 to 26. For clarity, reference numerals for comparable features have been kept consistent across the two embodiments.

Figure 17:
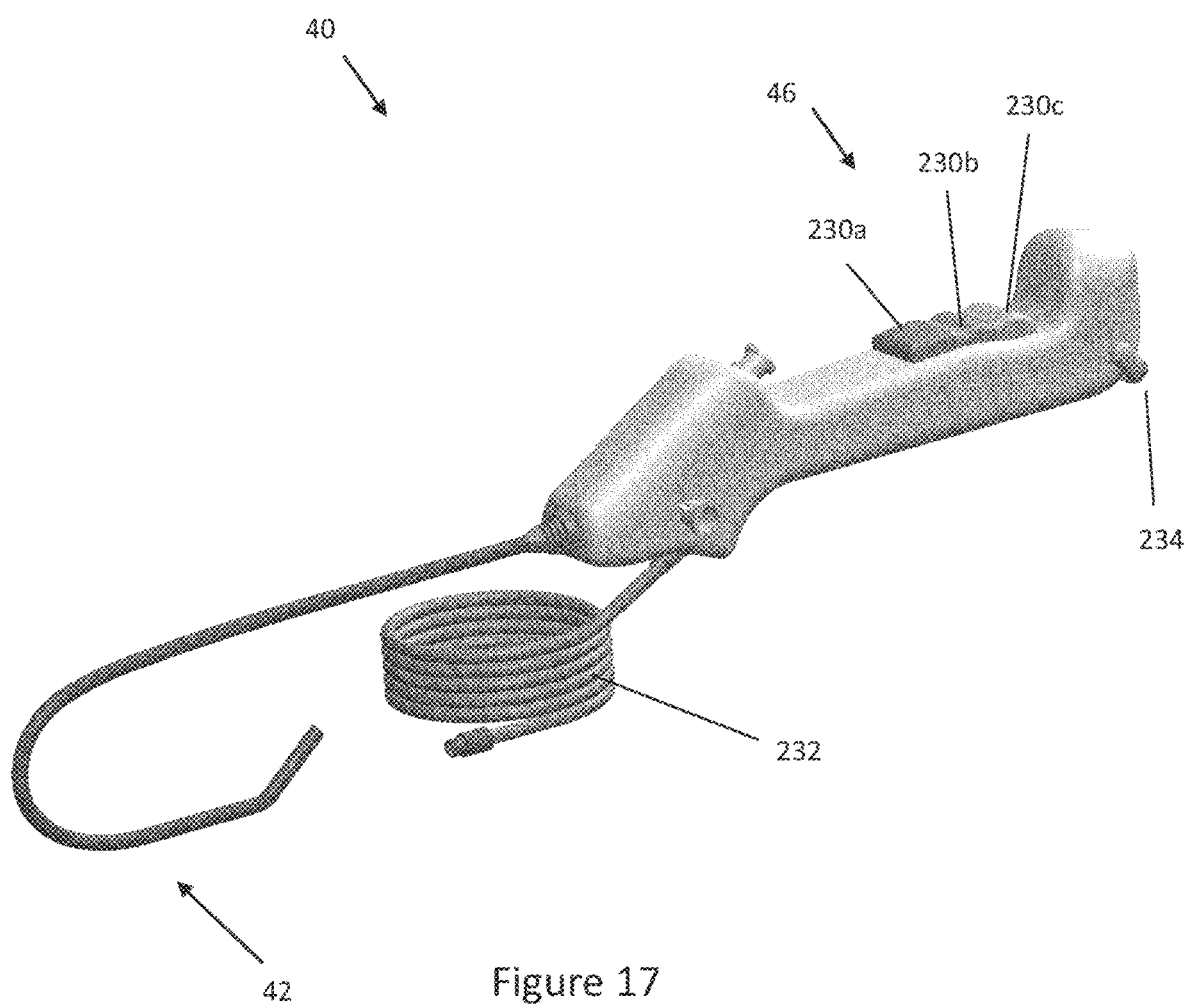
FIG. 17 is a perspective view of a delivery device according to a further embodiment of the invention.

FIG. 17 shows a perspective view of the delivery device 40 according to the further embodiment. The delivery device 40 comprises a handle 46 operatively connected to a flexible delivery tube 42. The delivery tube 42 is configured to at least partially receive the expander 10 in a compressed state and to position and deploy the expander 10 within the prostatic urethra 30 of a patient. The delivery tube 42 is similar to the previous embodiment in that it comprises an inner tube 50 surrounded by an outer sleeve 48 movable between a storage position, a partially-deployed position and a fully-deployed position. However, the delivery device shown in FIG. 17 further comprises an intermediate steering tube that surrounds the inner tube 50 and is in turn surrounded by the outer sleeve 48. The steering tube is not shown in FIG. 17 but is described in further detail below.

The flexibility of the delivery tube 42 shown in FIG. 17 is beneficial as the delivery tube 42 can bend and flex to conform to the path of the patient's urethra, thereby reducing any discomfort experienced by the patient. The steering tube allows the position and inclination of the distal tip region 44 to be controlled and steered, which beneficially assists in the insertion and positioning of the delivery tube 42 within the patient. Furthermore, the steerable delivery tube 42 allows the imaging device 90 of the delivery tube 42 to be moved to provide a wider field of view to the clinician.

Figure 18:
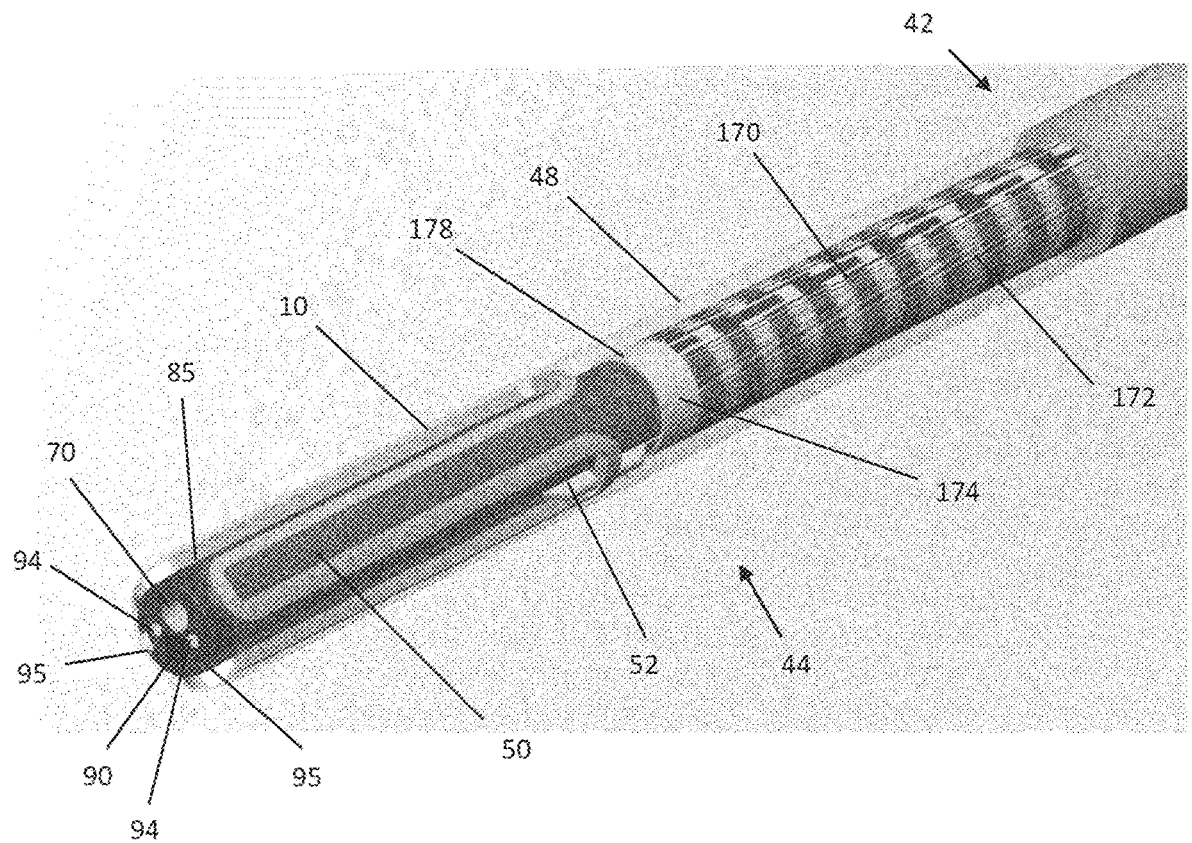
FIG. 18 is a perspective view of the distal tip of the delivery device of FIG. 17.

FIG. 18 is a perspective view of the distal end region 44 of the delivery tube 42. The distal end region 44 of the outer sleeve 48 has been shown as transparent in FIG. 18 for clarity. The distal end portion of the outer sleeve 48 is suitably of a rigid plastics material so that it can accommodate the outward radial force exerted by the expander 10 and keep the expander 10 in a stored position within the system. Conversely, the proximal portion of the outer sleeve 48 is suitability of a flexible plastics material and may, for example, consist of or comprise a braided sheath. At least a proximal portion of inner tube 50 is also of flexible plastics and may also consist of or comprise a braided sheath.

FIG. 18 shows the steering tube 170 surrounding the inner tube 50 and surrounded by the outer sleeve 48. The steering tube 170 is an elongate flexible plastics tube with a braided distal end 172. The steering tube 170 is operable by a clinician via the handle 46 to vary the position and inclination of the distal tip region 44 and thus the expander 10. Furthermore, in this embodiment, the retention features 52 are secured to and extend distally from the braided distal end 172. The retention features 52 are configured to engage the expander 10 and to prevent longitudinal or circumferential movement of the expander 10 relative to the steering tube 170.

Figure 19:
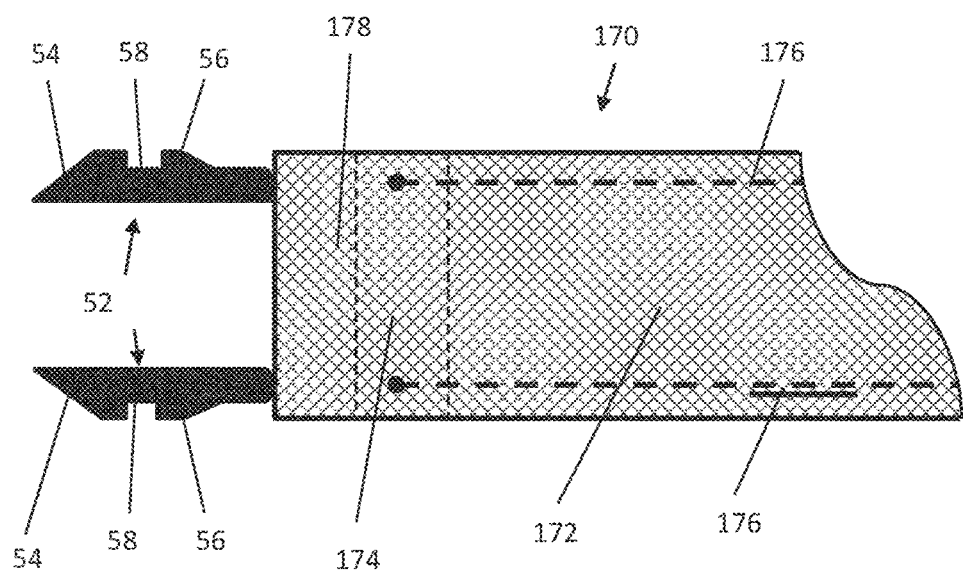
FIG. 19 is a schematic side view of the distal end region of a steering tube of the delivery device of FIG. 17.

The distal end of the steering tube 170 shown schematically in FIG. 19 with the inner tube 50 and the outer sleeve 48 removed for clarity. The steering tube 170 comprises a steering ring 174 at the distal end 178 of the braided portion 172. Two steering wires 176 are connected to opposing sides of the steering ring 174 and extend proximally along the length of the steering tube 170 to the handle 46. The steering wires 176 are operably coupled to the handle 46 whereby a clinician may vary the tension in the steering wires 176. This causes the position and inclination of the steering ring 174, and thus the expander 10, to be controlled by a clinician operating the handle 46.

The flexibility of the proximal portion of the outer sleeve 48 and the flexibility of the inner tube 50 are such that they can accommodate and allow the deflected angle of the steering tube 170 without kinking or increasing the deflection force required by the steering wires 176.

The steering tube 170 further comprises two retention formations 52 for retaining the expander 10 in the delivery tube 42. The retention formations 52 are elongate tabs that extend distally from the distal end 178 of the braided portion 172 such that the retention formations 52 protrude from the end of the steering tube 170. The retention formations 52 each comprise a retention slot 58 for retaining the expander 10 and are spaced angularly about the steering tube 170 such that the expander 10 is oriented to align with the prostatic lobes when the delivery tube 42 is inserted into the prostatic urethra 30.

As shown in FIG. 19, the retention formations 52 each comprise a proximal protrusion 56 and a distal protrusion 54 with a retention slot 58 defined between them. The retention slot 58 is configured to at least partially receive a proximal end 16 of the expander 10, thereby inhibiting longitudinal or circumferential movement of the expander 10 relative to the inner tube 50. When the outer sleeve 48 surrounds the retention formations 52, for example in the storage or partially-deployed configuration, the outer sleeve 48 surrounds the retention formations 52 and prevents the expander 10 from expanding radially and hence disengaging the retention formations 52.

The inner tube 50 is movable longitudinally relative to the steering tube 170 between a distal position as shown in FIG. 18 and a proximally retracted position. When in the retracted position, the distal tip 72 of the inner tube 50 is located between the proximal end 16 and the distal end 13 of the expander 10, Moving the inner tube 50 between the distal position and the retracted position beneficially changes the longitudinal position of the imaging chip 92 relative to the expander 10. Specifically, when the inner tube 50 is in the distal position, the imaging chip 92 is positioned distally of the distal end 13 of the expander 10 such that expander is not within the field of view of the imaging chip 92. Conversely, when the inner tube 50 is in the retracted position, the distal end of the expander 10 is within the field of view of the imaging chip 92. This beneficially allows the distal end 13 of the expander 10 to be imaged relative to the anatomy within the prostatic urethra 30.

As shown in FIG. 18, the inner tube 50 comprises two grooves 95 extending longitudinally in a proximal direction from the distal tip 72 of the inner tube 50. The grooves 95 are configured to at least partially receive the retention formations 52. This is advantageous as the grooves 95 accommodate some of the thickness of the retention formations 52 and so reduce the overall diameter of the delivery tube 42. Furthermore, the grooves 95 allow and guide movement of the inner tube 50 relative to the steering tube 170 between the distal position and the retracted position.

Figure 20:
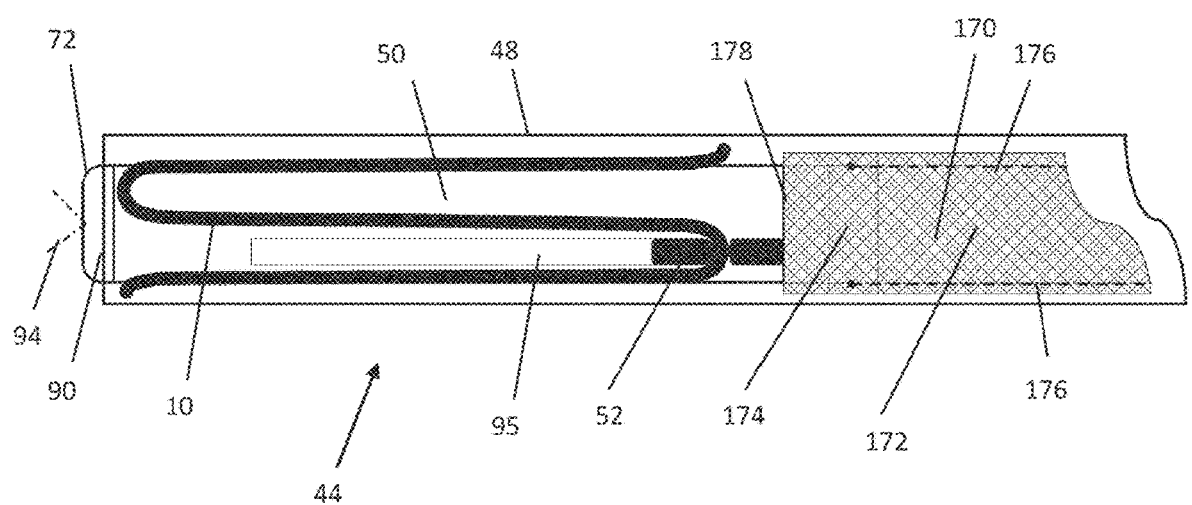
FIG. 20 is a schematic view of the distal end region of the delivery device of FIG. 17 in the stored configuration.

FIG. 20 is a schematic view of one embodiment of the distal end region 44 of the delivery tube 42 in the storage configuration. When in the storage configuration, the inner tube 50 is in the distal position and the outer sleeve 48 is in the storage position surrounding the expander 10. The distal tip 72 of the inner tube 50 extends distally with respect to the distal end of the outer sleeve 48 when the inner tube 50 is in the distal position. This beneficially allows the imaging chip 92 to capture images of the anatomy that are not obscured by the expander 10 or the outer sleeve 48.

Furthermore, the distal end portion of the inner tube 50 is of rigid plastics to support the expander 10 along its length when the inner tube 50 is in the distal position. When the delivery tube 42 is being inserted into, and along, the urethra, the inner tube 50 thereby prevents the expander 10 deflecting inwardly which could otherwise cause the expander 10 to disengage from the retention formations 52 prematurely.

Figure 21:
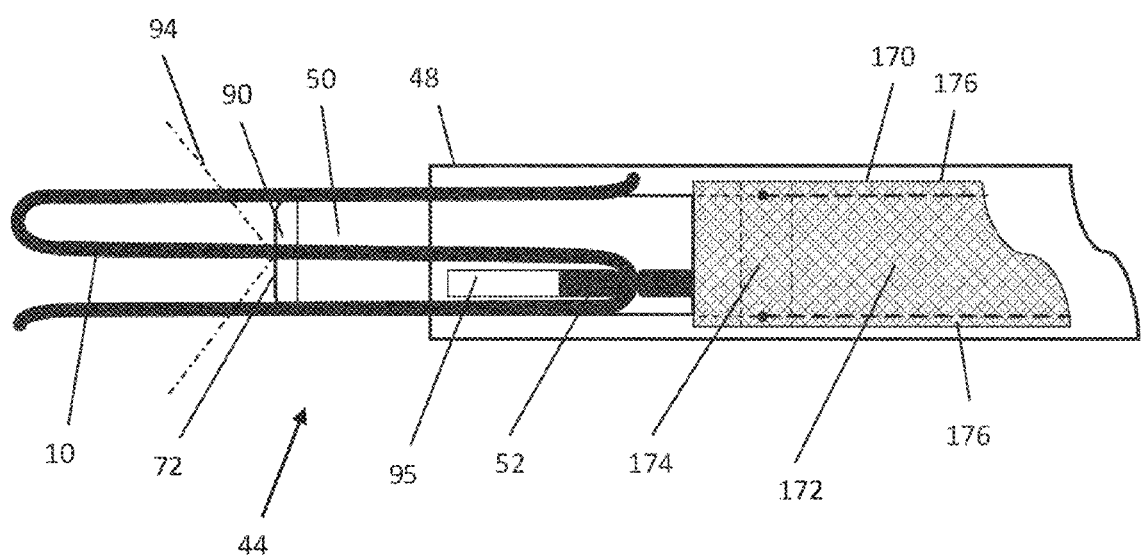
FIG. 21 is a schematic view of the distal tip of the delivery device of FIG. 17 in the partially-deployed configuration.

Turning now to FIG. 21, the delivery tube 42 is shown here in the partially-deployed configuration. In the partially-deployed configuration, both the inner tube 50 and the outer sleeve 48 have been moved proximally relative to the expander 10 such that the distal end 13 of the expander is now unsheathed. Furthermore, the inner tube 50 is in the retracted position such that the distal tip 72 of the inner tube 50 is located at a longitudinal position between the proximal and distal ends of the expander 10. As shown in FIG. 21, when the delivery tube 42 is in the partially-deployed configuration, the distal end of the outer sleeve 48 is located proximally relative to the distal tip 72 of the inner tube 50 and distally relative to the retention formations 52. The outer sleeve 48 therefore retains the expander 10 in the stored configuration whilst not obscuring the field of view of the imaging chip 92.

Figure 22:
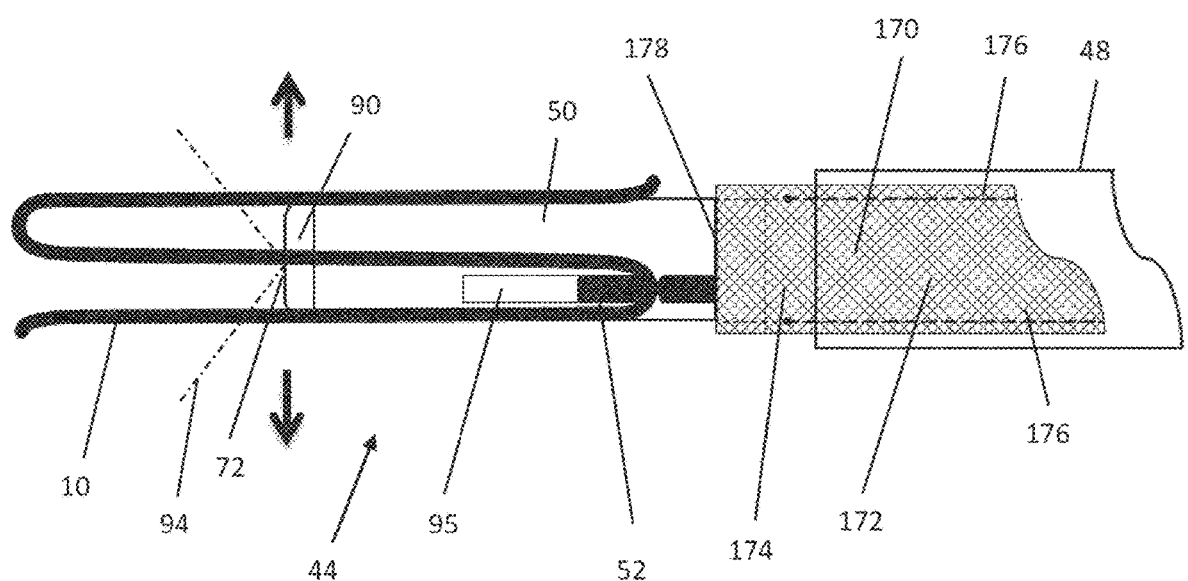
FIG. 22 is a schematic view of the distal tip of the delivery device of FIG. 17 in the fully-deployed configuration.

FIG. 22 is a schematic view of the distal end region 44 of the delivery tube 42 in the fully-deployed configuration. In the fully-deployed configuration, the outer sleeve 48 is moved proximally to the extent that its distal end is located proximally with respect to the retention features 52. This fully uncovers the expander 10 and allows the expander 10 to expand radially, thereby to disengage from the retention formations 52.

Figure 23:
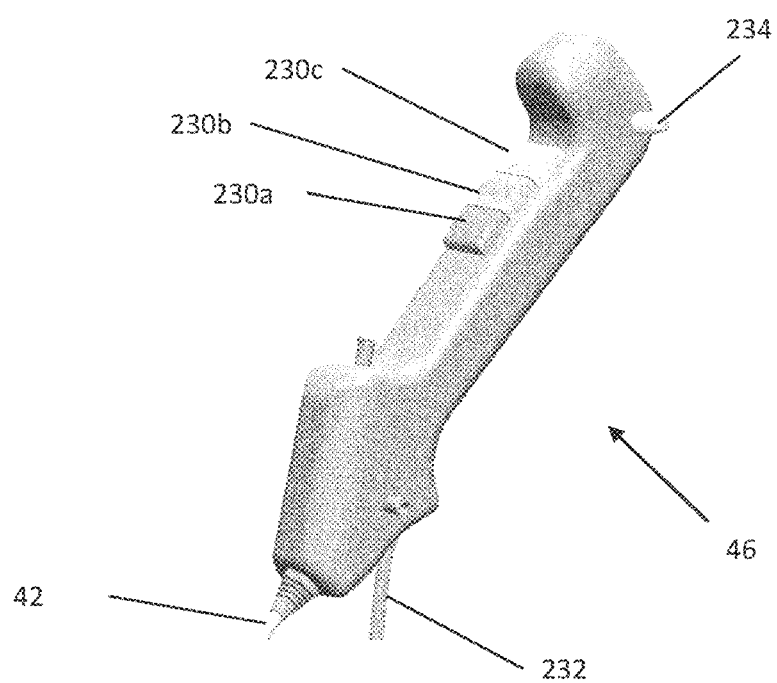
FIG. 23 is a perspective view of the handle of the delivery device of FIG. 17.

Turning now to FIG. 23, this shows a perspective view of the handle 46. The handle 46 comprises three buttons 230a, 230b, 230c that are operable by the clinician to reconfigure the delivery tube 42 between the storage, partially-deployed and fully-deployed configurations as outlined in FIGS. 20 to 22. The buttons 230a, 230b, 230c allow the clinician to adjust the delivery tube 42 easily between the various configurations. The handle 46 further comprises a lever 234 that is connected to the steering wires 176. The lever 234 may be operated to vary the tension in the wires and thus to control the position and inclination of the distal end of the steering tube 170.

The handle 46 may further comprise a lever or button that can lock the delivery tube 42 in a desired configuration. This prevents the clinician inadvertently reconfiguring the delivery tube 42 to the partially-deployed or fully deployed configuration before the expander 10 is positioned correctly in the patient's anatomy.

The handle 46 of FIG. 23 further comprises an irrigation tube 232, also shown in FIG. 17.

Figure 24:
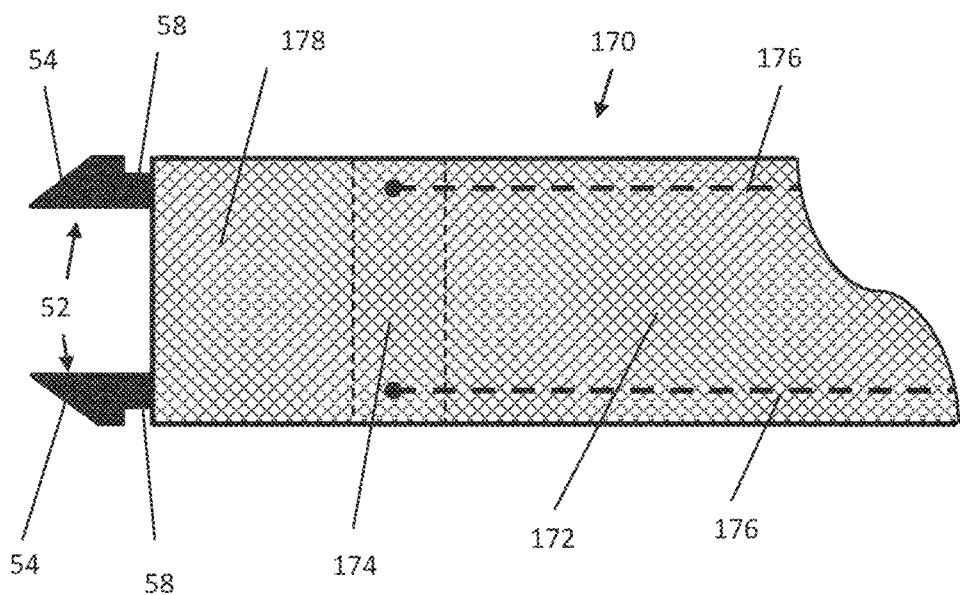
FIG. 24 is a schematic side view of the distal end region of a steering tube according to another embodiment.

FIG. 24 shows an alternative embodiment of the steering tube 170. In FIG. 24, the retention features 52 extend from the distal end 178 of the steering tube 170, for example being connected to, and extending distally from, the steering ring 174. Each retention feature 52 comprises a distal protrusion 54. In this example, the retention slot 58 is defined between the distal protrusion 54 and the distal end 178 of the braided portion 172 of the steering tube 170. The expander 10 may be at least partially received within the retention slot 58 as before.

Figure 25:
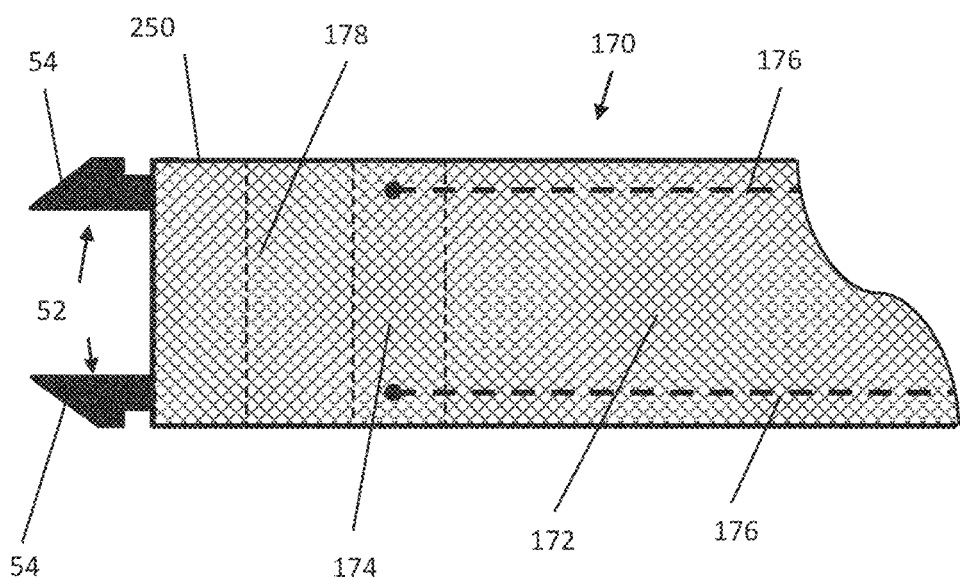
FIG. 25 is a schematic side view of the distal end region of a steering tube according to another embodiment.

FIG. 25 shows a further embodiment of the steering tube 170. In FIG. 25, the retention features 52 extend from the distal end of the steering tube 170 as described above in relation to FIG. 24. However, in this case the retention features 52 are attached to and extend from a retaining ring 250. The retention features 52 and the retaining ring 250 may form a discrete sub-assembly that can be coupled to the steering ring 174 of the steering tube 170.

Figure 26:
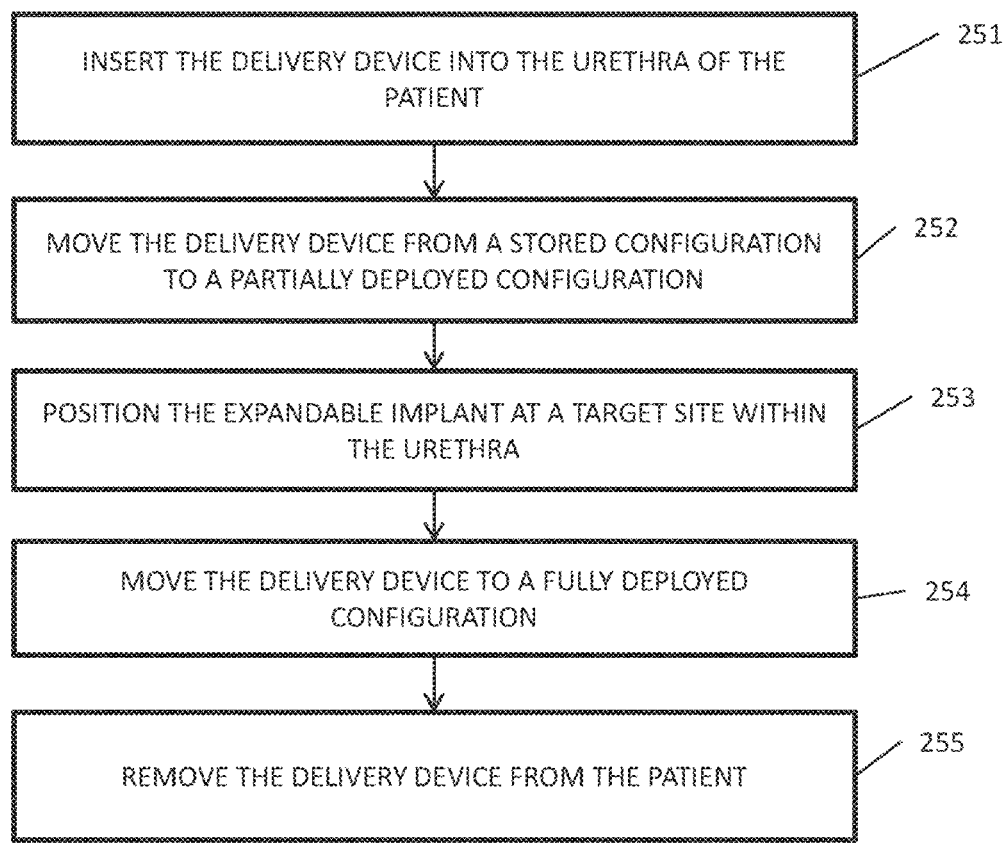
FIG. 26 is a flow chart outlining the steps of deploying an expandable implant using the delivery device of FIG. 17.

Turning now to FIG. 26, a flow chart outlining a method of deploying the expandable implant 10 within the prostatic urethra 30 is shown. In the first Step 251, the delivery tube 42 of the delivery device 40 is inserted into the patients urethra via the penis. The delivery tube 42 is inserted in the storage configuration in which the outer sleeve 48 surrounds the expander 10 thereby retaining the expander 10 in the stored configuration. The clinician may operate the handle 46 to control the steering ring 174 and adjust the angle of the distal tip region 44 of the delivery tube 42 to aid insertion of the delivery tube 42 into and along the urethra.

The distal end of the delivery tube 42 is advanced along the urethra until it reaches the bladder neck 32. In Step 252, the delivery tube 42 is reconfigured from the storage configuration to a partially-deployed configuration. In the partially-deployed configuration, the inner tube 50 is retracted so that the imaging chip 92 at the distal end of the inner tube 50 may view the distal end 13 of the expander 10. Furthermore, the outer sleeve 48 is also retracted such that the distal end 13 of the expander 10 is unsheathed but the proximal end 16 of the expander 10 remains sheathed and retained on the retention formations 52.

In Step 253 the clinician positions the expander 10 at a target site in the prostatic urethra 30 by moving the distal end region 44 of the delivery tube 42 in a proximal direction from the bladder neck 32 with the aid of graduation marks on the delivery tube 42 to indicate the axial distance travelled from the bladder neck 32. The bladder neck 32 may thereby be used as a datum for positioning the expander 10 longitudinally within the prostatic urethra 30. When satisfied that the distal end region 44 and thus the expander 10 are in the correct longitudinal position, the clinician may then rotate the delivery device 40 to orient the expander 10 at the target site. The expander 10 is oriented such that the distal apices 15 of the expander 10 that are visible on the image captured by the imaging device 90 are aligned with the prostatic lobes around the prostatic urethra 30.

As before, the clinician may move the delivery tube 42 further in a distal direction when the expander 10 is in the correct orientation so that the verumontanum 25 comes into view. The expander 10 can thereby be placed in a clinically-acceptable position between the bladder neck 32 and verumontanum 25, with the apices circumferentially targeting the lateral lobes.

In Step 254, when the clinician is satisfied with the position of the expander 10, the outer sleeve 48 is retracted to the fully-deployed position such that the expander 10 is deployed within the prostatic urethra 30. Finally, in Step 255, the delivery tube 42 is removed from the urethra. The delivery tube 42 may be withdrawn in the fully-deployed configuration or preferably the clinician reconfigures the delivery tube 42 to the partially-deployed or storage configurations. In all configurations, but most effectively in the storage configuration, the clinician may use the imaging chip 92 to view the deployed expander 10 to confirm that the expander 10 has been deployed correctly within the prostatic urethra 30.

It will be appreciated that various changes and modifications can be made to the present invention without departing from the scope of the present application. For example, the intermediate tube 170 to which the expander 10 is directly or indirectly fixed need not necessarily have steering functionality.

Turning finally to FIGS. 27 to 31, these drawings show further details of a practical embodiment of the invention.

Figure 27:
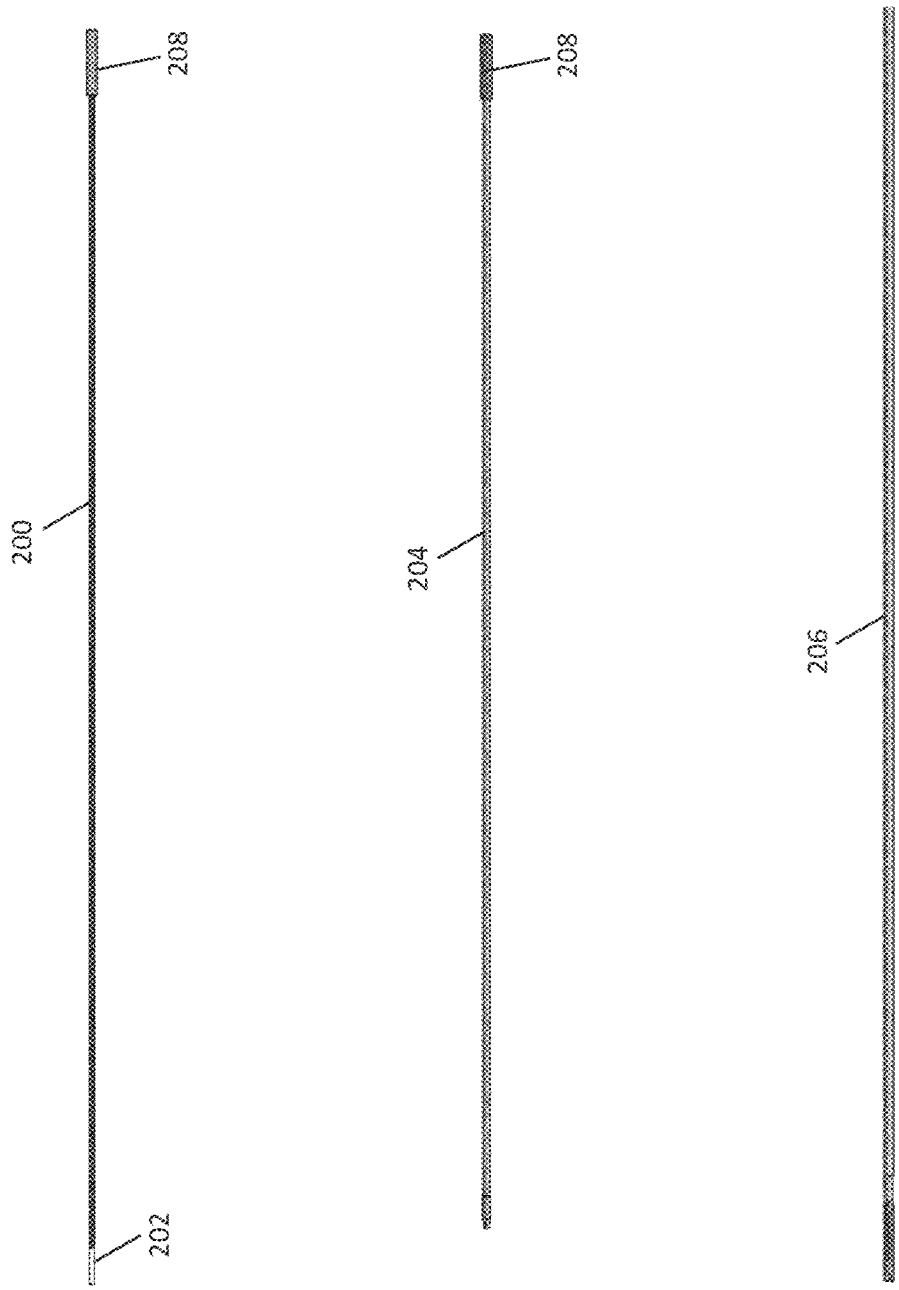
FIG. 27 shows three elongate elements of a delivery sheath of a delivery device of the invention, namely an imaging sheath with a rigid camera tip, a steering sheath surrounding the imaging sheath and an outer sheath surrounding the imaging sheath and the steering sheath.

FIG. 27 shows three elongate elements of a delivery sheath forming part of a delivery system of the invention. These three elongate elements of the delivery system are concentrically-aligned sheaths, namely: an innermost imaging sheath 200 with a rigid camera tip 202 that exemplifies an imaging head, an inner or intermediate steering sheath 204 surrounding the imaging sheath 200; and an outer sheath 206 surrounding the imaging sheath 200 and the steering sheath 204. All of the sheaths 200, 204, 206 are tubular in this example although, in principle, the imaging sheath 200 could be a solid but flexible rod with any wiring, cabling or ducting for the camera tip 202 embedded within it, for example in respective parallel channels of an extruded profile. In any event, any such wires or cables must be isolated from each other and from any flow of irrigating liquid that is conveyed along the imaging sheath 200.

The sheaths 200, 204, 206 must be as thin as possible to ensure that the overall diameter of the delivery sheath assembly is advantageously small, for example with an outer diameter of less than sixteen French (5.33 mm) in the application described. As a non-limiting illustrative example, the outer sheath 206 may have a wall thickness of about 0,175 mm whereas the main proximal section of the steering sheath 204 may have a wall thickness of about 0.71 mm, allowing about 0.61 mm for the expander 10 and for clearance. The wall thickness of the imaging sheath 200 under the expander 10 may, for example, be about 0.195 mm.

The sheaths 200, 204, 206 are flexible enough to permit an angle of deflection of, say, 40 to 90 degrees so as to accommodate the curvature of the male urethral anatomy and to access the prostatic urethra. In particular, the sheaths 200, 204, 206 must be capable of flexing along their length as they extend along the male urethra from the point of insertion at the penile meatus through to the bladder neck. The sheaths 200, 204, 206 therefore each have a flexible steering section to provide for deflection driven by a steering mechanism controlled by a handle (not shown) at the proximal end of the delivery sheath. The sheaths 200, 204, 206 also each have a flexible proximal section to provide for deflection imposed by the anatomy, for example to track through the curvature of the penile canal. For example, one or more of the sheaths 200, 204, 206 may be braided for flexibility to accommodate curvature of the anatomy and deflection of the imaging tip, but the structure must also be stiff enough axially and circumferentially to resist the forces of insertion, steering, navigation, unsheathing of the expander 10 and, if necessary, re-sheathing of the expander 10. As explained below, any or all of the sheaths 200, 204, 206 may have tailored stiffness and flexion properties for these purposes.

The torsional stiffness of the sheaths 200, 204, 206 must be sufficient to allow for angular alignment of the expander 10 about the longitudinal axis. In this respect, the circumferential or angular positioning of the expander 10 is controlled by global rotation of the handle. The handle thereby applies torque to the sheaths 200, 204, 206 attached to it, noting that the sheaths 200, 204, 206 are fixed against circumferential angular movement relative to the handle and so cannot rotate independently of the handle.

Each sheath 200, 204, 206 has a hub 208 on its proximal end, shown here only on the imaging sheath 200 and the steering sheath 204, that allows the sheath to slot into a specific axial position in the handle. The hubs 208 lock the respective sheaths 200, 204, 206 within the system in such a way that prevents them from moving in any direction except axially along a fixed travel path, as controlled by a clinician operating the handle.

The simplest and most basic form of sheath would be a single extrusion comprising a polymer material of a certain durometer value. However, a single material extrusion with the necessarily thin wall thickness may present a technical challenge as it could kink or buckle when deflected by a steering mechanism, or under axial compression, or under other bending loads. For this reason, any or all of the sheaths 200, 204, 206 may benefit from differential material properties along their length to provide the individual sheaths, and the stacked sheath assembly, with the design characteristics required to access the prostatic urethra, to navigate the anatomy, and to steer and support the expander 10.

Examples of characterisation properties to be tailored along the length of a sheath 200, 204, 206 may include: flexibility; kink resistance; trackability; the ability to apply axial force parallel to the longitudinal axis—i.e. 'pushability'; and the ability to apply torque about the longitudinal axis—i.e. 'torquability'. Tailoring may, for example, be achieved by the following options:

Hybrid extrusion, in which two materials of differing stiffness or durometer properties are joined together by reflows or joints.

A fully-braided sheath, this being a custom multi-layered braided sheath with a specific pitch design or angle of braid that is tailored to the stiffness properties required. Braiding may be uniform along its length.

A hybrid braided sheath, this also being a custom multi-layered braided sheath with a specific pitch design or angle of braid tailored to the stiffness properties required. However, in this case, braiding is varied along its length, for example with tighter and looser braids, or denser and less dense braids, at different longitudinal positions where the sheath is required to be more or less flexible. The angle of the braids relative to central longitudinal axis can also be varied to adjust flexibility along the length of a sheath.

A rigid tip moulded section may be reflowed or overmoulded onto a braided sheath.

Figure 28:
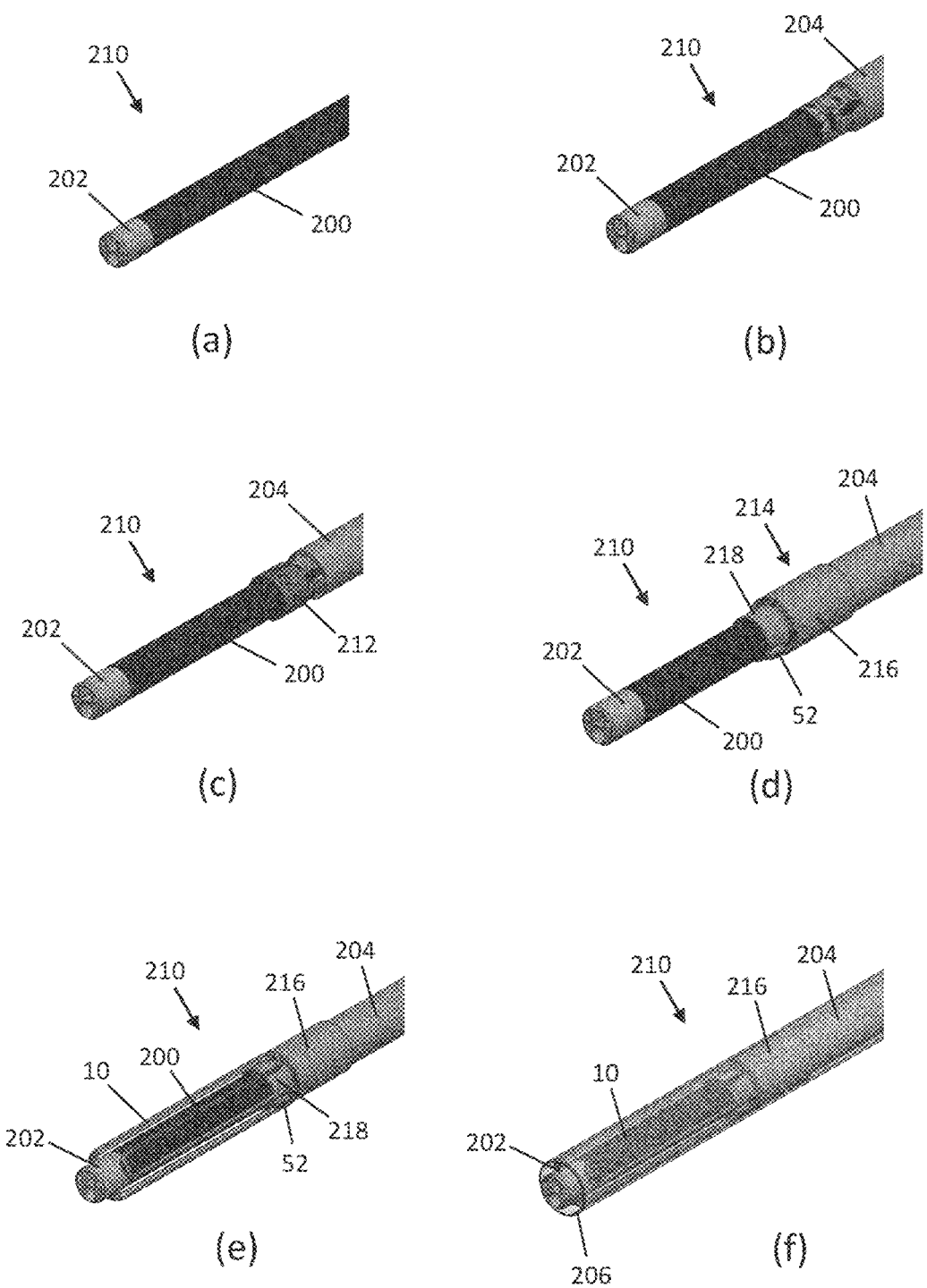
FIG. 28 is a series of enlarged detail perspective views showing components of a distal tip portion of the delivery sheath of FIG. 27.

FIG. 28 is a series of views showing components of a distal end portion 210 of the delivery sheath of FIG. 27 as a stack-up assembly, working radially outwardly in sequence from the inside out.

FIG. 28(a) shows the braided imaging sheath 200 with the rigid camera tip 202. The camera tip 202 has image-sensing and lighting features like those shown in FIG. 13, in addition to an irrigation channel or duct that extends along the imaging sheath 202 and terminates at the distal tip. The irrigation duct may be fluidly connected to a Luer connector on the handle whereby liquid can travel down the imaging sheath 200 from the proximal end.

FIG. 28(b) shows the steering sheath 204 that lies on and surrounds the imaging sheath 200 and terminates at the proximal end of the distal end portion 210, hence being spaced from the distal tip to leave a distally-protruding portion of the imaging sheath 200 exposed.

FIG. 28(c) shows a pull ring 212 added to the distal end of the steering sheath 204 and FIG. 28(d) shows an implant holder 214 added to the distal end of the steering sheath 204 around the pull ring 212. The pull ring 212 and the implant holder 214 lie at the interface between the imaging sheath 200 and the steering sheath 204 and permit longitudinal movement of the imaging sheath 200 relative to the steering sheath 204. In particular, the imaging sheath 200 slides longitudinally within and with respect to the steering sheath 204, the pull ring 212 and the implant holder 214.

The pull ring 212 and the implant holder 214 will be described in more detail with reference to FIG. 30. For now, it will be noted that the proximal end portion of the implant holder 214 is radially oversized relative to the diameter of the steering sheath 204, thus defining a cylindrical bearing surface 216 that stands proud of the steering sheath 204. It will also be noted that the implant holder 214 has a longitudinally-stepped profile such that its distal end portion is narrower than its proximal end portion, defining a distal support surface 218 from which a pair of lugs serving as retention formations 52 project radially as described previously.

FIG. 28(e) shows an implant in the form of an expander 10 now added to surround the exposed portion of the imaging sheath 200 that protrudes distally from the steering sheath 204. The thickness of the wire of the expander 10 is less than the step change in the diameter of the implant holder 214 between the bearing surface 216 and the support surface 218. The expander 10 extends from a proximal end where it is supported by the support surface 218 of the implant holder 214 to a distal end where it is supported by the camera tip 202. The expander 10 is held against axial and circumferential movement relative to the steering sheath 204 by the retention formations 52.

FIG. 28(f) shows the outer sheath 206 now added to surround all of the aforementioned components. The outer sheath 206 is shown here advanced distally relative to the steering sheath 204 and the expander 10 into the storage position that retains and enshrouds the expander 10. Despite being thin-walled, the outer sheath 206 must constrain the crimped expander 10 without deforming excessively. Optionally, therefore, the outer sheath 206 could have a relatively rigid section at its distal tip to constrain the crimped expander 10, adjoining a relatively flexible proximal section forming most of the length of the outer sheath 206.

It will be apparent that longitudinal sliding movement of the outer sheath 206 relative to the steering sheath 204 is guided and facilitated by sliding on the bearing surface 216 of the implant holder 214. This minimises the area of sliding contact, and hence friction, and maintains concentricity between the sheaths 200, 204, 206.

In this example, the distal extremity of the camera tip 202 with its image-capturing and lighting components, such as a CMOS chip and LEDs adjacent an irrigation duct, protrudes distally from the distal end of the outer sheath 206. This ensures the best possible field of view as the delivery sheath navigates the anatomy before deployment of the expander 10. However, in other examples, the distal extremity of the camera tip 202 could be substantially level with the distal end of the outer sheath 206 or could even be recessed proximally to a small extent.

Figure 29:
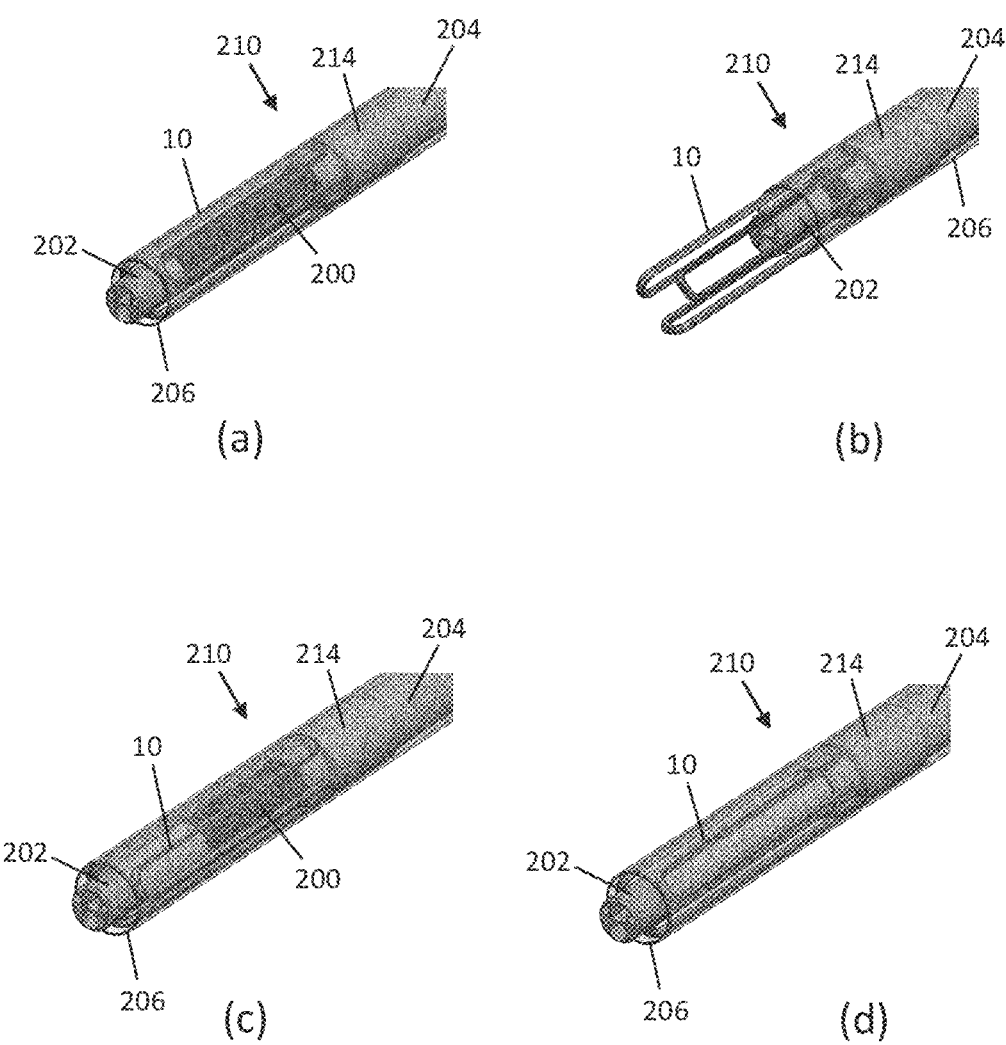
FIG. 29 is a selection of enlarged detail views of a distal tip portion of the delivery sheath of FIG. 27, showing variants in the length of the rigid camera tip of the imaging sheath.

The various views of FIG. 29 show the distal end portion 210 of the delivery sheath and illustrate variants in the length of the rigid camera tip 202, parallel to the longitudinal axis of the delivery sheath.

FIGS. 29(a) and 29(b) show a short camera tip 202 as also shown in the views of FIG. 28, in the storage and partially-deployed configurations respectively. Correspondingly, the camera tip 202 is shown in advanced and retracted positions in FIGS. 29(a) and 29(b) respectively. In this example, the length of the camera tip 202 is about one quarter of the overall length of the expander 10. A correspondingly long portion of the more flexible imaging sheath 200 is exposed beyond the distal end of the steering sheath 204 and underlies the expander 10.

FIG. 29(b) shows how, in the partially-deployed configuration, the outer sheath 206 and the imaging sheath 200, including the camera tip 202, are pulled back proximally relative to the steering sheath 204 and hence also relative to the expander 10. Thus, beneficially, the image capture device of the camera tip 202 when in the retracted position can visualise the expander 10 against a backdrop of the adjacent anatomy, from a viewpoint within the expander 10.

FIGS. 29(c) and 29(d) show longer camera tips 202 than that shown in FIGS. 29(a) and 29(b), both views being of the distal end portion 210 in the storage configuration in which the expander 10 is covered fully by the outer sleeve 206, in FIG. 29(c), the length of the camera tip 202 is about half of the overall length of the expander 10. A correspondingly shorter portion of the imaging sheath 200 is exposed beyond the distal end of the steering sheath 204. In FIG. 29(d), the camera tip 202 extends substantially the entire length of the expander 10. In that case, none of the imaging sheath 200 is exposed beyond the distal end of the steering sheath 204.

Thus, by varying the length of the camera tip 202 relative to the more flexible imaging sheath 200, the support that underlies the expander 10 can be tailored to have differential stiffness along its length. This may, for example, help to accommodate movement of the imaging sheath 200 through the deflected steering sheath 204, noting that the imaging sheath 200 must move within the deflected section of the steering sheath 204 that surrounds it and so must be flexible enough to accommodate its deflected curvature. Conversely; during re-sheathing, the distal end of the camera tip 202 must be pushed back to its start position through the distal apices of the expander 10 to return to the distal tip of the delivery sheath. The camera tip 202 must be supported securely enough to undergo this distal movement without deflection or buckling of the structure that supports the camera tip 202.

Potentially; the stiffness of the imaging sheath 200 can be tailored to vary along its length—for example, with tailored braiding comprising braided elements of varying density, pitch, angle and/or thickness—so as to provide stable support for the expander 10 and yet to navigate easily around the deflected steering sheath 204.

Figure 30:
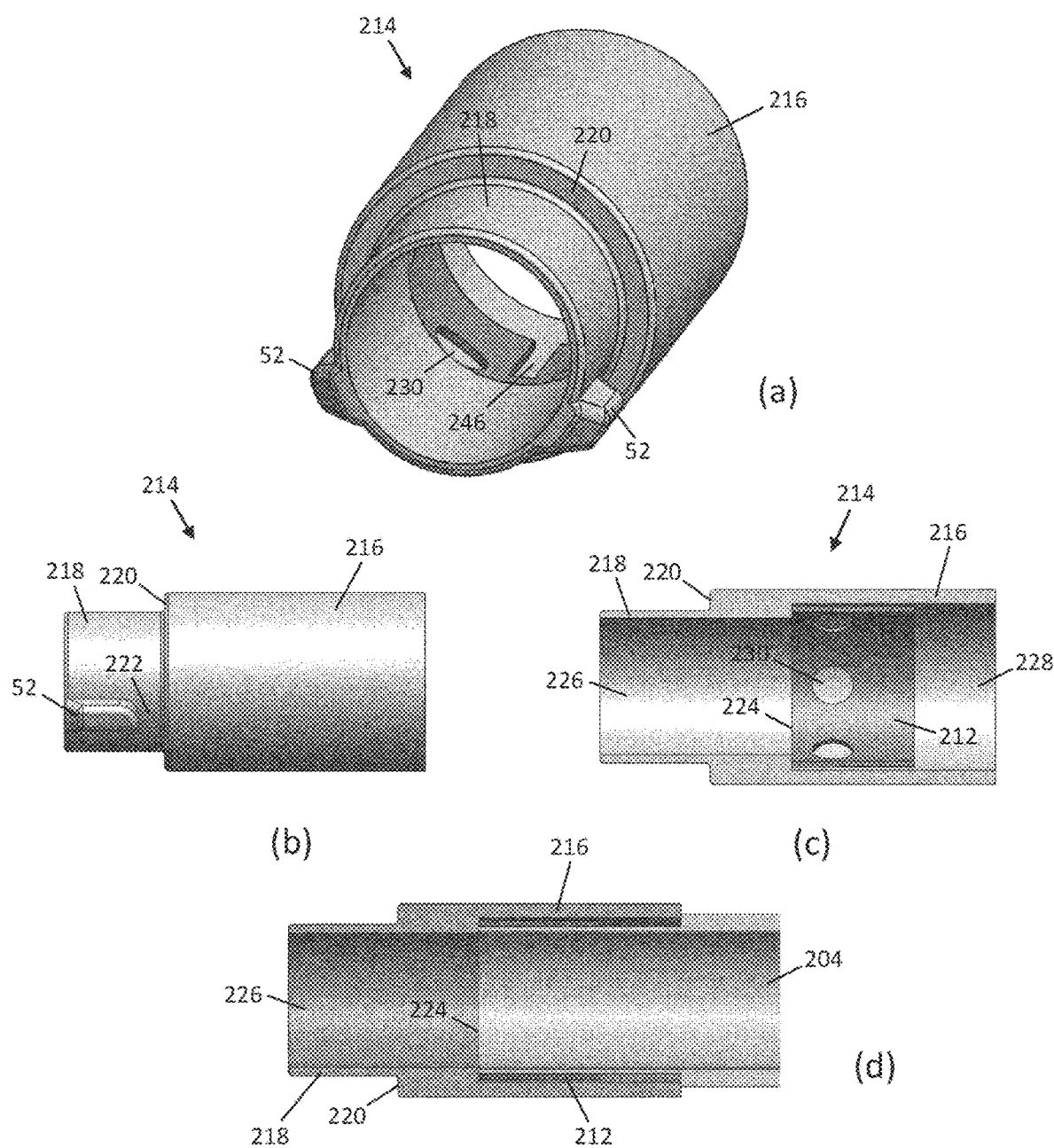
FIG. 30 is a selection of views of an implant holding component and steering/pull ring assembly of the delivery sheath of FIG. 27.

The various views in FIG. 30 show the assembly of the pull ring 212 and the implant holder 214 in more detail. As best seen in FIGS. 30(a) and 30(b), a circumferential step 220 effects the aforementioned change in external diameter between the bearing surface 216 and the support surface 218 of the implant holder 214. FIG. 30(a) shows that the height or radial protrusion of the retention formations 52 is the same as, or slightly less than, the height of the step 220.

Each retention formation 52 is spaced distally from the step 220 to define a gap or slot 222 that can accommodate a respective proximal apex of the expander 10 held by the outer sleeve 206 (not shown) against the support surface 218. The step 220 therefore serves as a proximal retention formation that cooperates with each retention formation 52.

Internally, as best seen in the longitudinal sectional views of FIGS. 30(c) and 30(d), the implant holder 214 has a circumferential shoulder 224 that effects a step change in the diameter of its longitudinal lumen from a narrow distal portion 226 to a wider proximal portion 228. The internal diameter of the distal portion 226 is a sliding fit with the external diameter of the imaging sheath 200 (not shown).

The proximal portion 228 of the implant holder 214 accommodates the pull ring 212 as an interference fit. The pull ring 212 could also, or alternatively, be secured in the implant holder 214 by a bonding process suitable for polymers such as reflow or over moulding. Adhesives and curing could also be used. The distal end of the pull ring 212 abuts the proximally-facing shoulder 224. The proximal end of the pull ring 212 lies distally with respect to the proximal end of the implant holder 214, FIG. 30(d) shows that a narrowed distal end portion of the steering sheath 204 is received and anchored within the pull ring 212. The internal diameter of the steering sheath 204 substantially matches that of the distal portion 226 of the implant holder 214 and so is also a sliding fit with the external diameter of the imaging sheath 200.

As shown in FIG. 30(c) and also in FIG. 30(a), the pull ring 212 has a circumferential array of angularly-spaced holes 230 to facilitate joining the steering ring to the implant holder though a bonding process and two longitudinal slots 246 (only one of which is shown) positioned on diametrically-opposed sides of the pull ring 212 for anchoring steering wires, not shown.

Thus, this example has an implant holding and steering feature that not only holds the expander 10 but can also steer the expander 10 and therefore the sheath that supports the expander 10, in this example the innermost imaging sheath 200 with its camera tip 202. In this respect, it is advantageous to steer from behind the expander 10, i.e. at a position that is proximal relative to the expander 10, so as to guide the expander 10 forward through the anatomy to the deployment location.

In proximal succession from the expander 10, therefore, the steering sheath 204 fitted with the pull ring 212 and the implant holder 214 provides: holding features that hold and orient the expander 10; a steering mechanism acting on a flexible steering section; and a flexible proximal section to track through the penile canal. In conjunction with the imaging sheath 200 and the outer sheath 206, the structure of the steering sheath 204 must provide sufficient tensile or axial strength for unsheathing and re-sheathing the expander 10 and to allow for deflection of the expander. The structure of the steering sheath 204 must also provide sufficient torsional strength for orienting the expander 10 angularly.

In the example shown, the implant holding feature is a moulded component that accommodates a pull ring for steering, being a separate component. However, in another embodiment, the implant holding feature and a pull ring or other steering formation could instead be integrated into one component.

Figure 31:
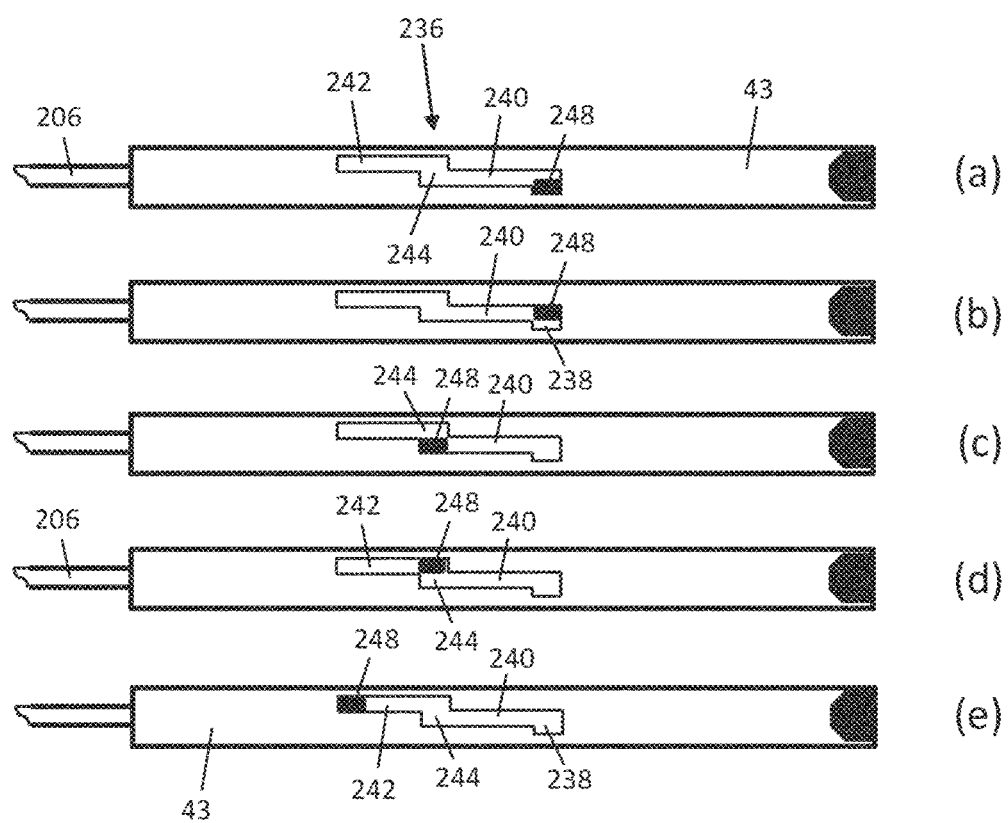
FIG. 31 is a series of schematic views showing the operation of an interlock mechanism for controlling relative movement of the elongate elements of a delivery sheath of the invention.

Finally, FIG. 31 shows, schematically, how an interlock mechanism can control relative axial movement of the sheaths 200, 204, 206 in some embodiments. In this example, that relative movement is permitted and controlled by a control element such as a pin 248 that can move along a path defined in this example by a slot 236, for example as the slot 236 moves relative to the pin 248. The slot 236 may, for example, be defined by the distal grip 43 of the handle 46, to which the imaging sleeve 200 and the outer sleeve 206 may be fixed, whereas the distal grip 43 may, for example, move relative to the steering sleeve 204 and to the pin 248 fixed to the steering sleeve 204.

The slot 236 is shaped to interact with the pin 248, defining a detent position that prevents longitudinal movement of the pin 248 and limited detent ranges within which longitudinal movement of the pin 248 is restricted. Movement of the pin 248 out of the detent positions or between and beyond those ranges is enabled only by deliberate relative angular movement between the pin 243 and the slot 236 about a longitudinal axis, for example by articulating a toggle in the handle 46. More generally, the imaging and outer sheaths 200, 206 can only move with articulation of components of the handle 46 which allow those sheaths 200, 206 to move through pre-calculated distances, respectively within and over the steering sheath 204, all in concentric relation.

In this example, the detent position is defined by a laterally-offset notch 238 at one end of the slot 236. The detent ranges are defined by a first section 240 of the slot 236 in series with a second section 242 of the slot 236. The second section 242 is offset laterally from the first section 240 by a laterally-extending kink or chicane 244 in the slot 236.

In a start position shown in FIG. 31(a), the pin 248 is received in the notch 238 that prevents longitudinal movement of the pin 248 along the slot 236. This prevents the distal grip 43 being moved toward the proximal grip 45 of the handle 46 and so locks the outer sleeve 206 in its distally-advanced storage position that secures the expander 10 against inadvertent deployment.

Moving the pin 248 laterally out of the notch 238 as shown in FIG. 31(*b*) allows the pin 248 to enter and move along the first section 240 of the slot 236, enabling the distal grip 43 to be pulled toward the proximal grip 45 in a first stage of movement. The pin 248 can move longitudinally along the first section 240 to an extent limited by the chicane 244, as shown in FIG. 31(*c*). In doing so, the outer sheath 206 and the imaging sheath 200 move proximally by a fixed axial distance toward the handle 46, into the partially-deployed position.

The outer sheath 206 and the imaging sheath 200 move together proximally and travel the same longitudinal distance relative to the steering sheath 204, which remains fixed against longitudinal movement relative to the handle 46. As described previously, this movement at least partially uncovers the expander 10 and allows the expander 10 to be imaged from the inside out, with the anatomy also in view.

Moving the pin 248 laterally through the chicane 244 as shown in FIG. 31(*d*) frees the pin 248 from the first section 240 of the slot 236 and allows the pin 248 to enter the second section 242 of the slot 240. The pin 248 can now move along the second section 242, enabling the distal grip 43 to be pulled further toward the proximal grip 45 in a second stage of movement. Longitudinal movement of the pin 248 along the second section 242 continues until the pin 248 encounters the opposite end of the second section 242, as shown in FIG. 31(*e*). By this stage, the outer sheath 206 has moved proximally by a further fixed distance into the fully-deployed position in which the expander 10 is uncovered completely, released from the system and therefore deployed.

Advantageously, resistance to lateral movement of the pin 248 must be overcome before the pin 248 can enter the notch 238, or exit the notch 238 into the first section 240 of the slot 236, or travel in either direction across the chicane 244 between the first and second sections 240, 242 of the slot 236. This helps to prevent inadvertent movement and provides touch feedback to the clinician to confirm the position of the pint relative to the various parts of the slot 236.

In another embodiment, an interlock mechanism may use rotary motion to drive or reciprocate the linear movement of the sheaths.

The invention claimed is:

1. A delivery device for deploying a self-expanding implant within a body cavity, the device comprising:
   at least one retention formation for holding the implant against axial or circumferential movement;
   an elongate longitudinally-extending outer element, radially outward of the at least one retention formation; and
   wherein the outer element is movable longitudinally relative to the at least one retention formation between:
      a storage position in which the outer element surrounds the implant and holds the implant engaged with the at least one retention formation; and
      a partial-deployment position in which the outer element uncovers a distal portion of the implant while surrounding a proximal portion of the implant to continue holding the implant engaged with the at least one retention formation;
   wherein the outer element is movable longitudinally, relative to the at least one retention formation, into a full-deployment position in which the outer element uncovers the proximal portion of the implant to an extent sufficient to disengage the implant from the retention formation for radial self expansion within the body cavity; and
   a handle configured to selectively control, disable and enable movement of the outer element into the full-deployment position; and
   an imaging head disposed on a longitudinal axis that extends on a radially-inward side of the at least one retention formation, wherein the imaging head is movable longitudinally between:
      an advanced position when the outer element is in the storage position; and
      a retracted position when the outer element is in the partial-deployment position,
   wherein the imaging head is configured to define a field of view, and wherein the field of view encompasses at least a distal end of the implant when the imaging head is in the retracted position, and
   wherein the imaging head defines a support surface that is configured to support at least the distal portion of the implant.

2. The device of claim 1, wherein the handle comprises a detent.

3. The device of claim 2, wherein the detent is configured to selectively control, disable and enable movement of the outer element from the storage position into the partial-deployment position.

4. The device of claim 2, wherein the detent comprises a path and an extension configured to follow the path, the path comprising a detent range beyond which movement of the extension in a longitudinal direction is restricted, the extension movable beyond the detent range by deliberate relative movement between the extension and the path.

5. The device of claim 4, wherein the deliberate relative movement is in a second direction transverse to the longitudinal direction.

6. The device of claim 2, wherein the handle is configured to selectively control, disable and enable movement of the imaging head.

7. The device of claim 1, further comprising an elongate longitudinally-extending inner element that defines a support surface and the at least one retention formation, wherein the inner element is configured for deflection at a steering section that is proximal with respect to the at least one retention formation.

8. The device of claim 1, wherein the at least one retention formation comprises a proximal protrusion and a distal protrusion defining a slot between them for at least partially receiving the implant.

9. The device of claim 1, the at least one retention formation is fixed relative to the handle and the outer elongate element and the imaging head are moveable axially relative to the handle.

10. A delivery device for deploying a self-expanding implant within a body cavity, the device comprising:
    at least one retention formation for holding the implant against axial or circumferential movement;
    an elongate longitudinally-extending outer element, radially outward of the at least one retention formation; and
    wherein the outer element is movable longitudinally relative to the at least one retention formation between:
       a storage position in which the outer element surrounds the implant and holds the implant engaged with the at least one retention formation; and
       a partial-deployment position in which the outer element uncovers a distal portion of the implant while surrounding a proximal portion of the implant to continue holding the implant engaged with the at least one retention formation;
wherein the outer element is movable longitudinally, relative to the at least one retention formation, into a full-deployment position in which the outer element uncovers the proximal portion of the implant to an extent sufficient to disengage the implant from the retention formation for radial self expansion within the body cavity;
a handle configured to selectively control, disable and enable movement of the outer element into the full-deployment position; and
an elongate longitudinally-extending inner element that defines a support surface and the at least one retention formation, wherein the inner element is configured for deflection at a steering section that is proximal with respect to the at least one retention formation.

11. The device of claim 10, wherein the handle comprises a detent.

12. The device of claim 11, wherein the detent is configured to selectively control, disable and enable movement of the outer element from the storage position into the partial-deployment position.

13. The device of claim 11, wherein the detent comprises a path and an extension configured to follow the path, the path comprising a detent range beyond which movement of the extension in a longitudinal direction is restricted, the extension movable beyond the detent range by deliberate relative movement between the extension and the path.

14. The device of claim 13, wherein the deliberate relative movement is in a second direction transverse to the longitudinal direction.

15. The device of claim 10, further comprising an imaging head disposed on a longitudinal axis that extends on a radially-inward side of the at least one retention formation, wherein the imaging head is movable longitudinally between:
an advanced position when the outer element is in the storage position; and
a retracted position when the outer element is in the partial-deployment position,
wherein the imaging head is configured to define a field of view, and wherein the field of view includes at least a distal end of the implant when the imaging head is in the retracted position.

16. The device of claim 15, wherein the handle is configured to selectively control, disable and enable movement of the imaging head.

17. The device of claim 10, wherein the at least one retention formation comprises a proximal protrusion and a distal protrusion defining a slot between them for at least partially receiving the implant.

18. The device of claim 10, wherein the at least one retention formation is fixed relative to the handle and the outer elongate element and an imaging head are moveable axially relative to the handle.

19. The device of claim 10, further comprising an imaging head disposed on a longitudinal axis that extends on a radially-inward side of the at least one retention formation, wherein the imaging head is movable longitudinally between:
an advanced position when the outer element is in the storage position; and
a retracted position when the outer element is in the partial-deployment position,
wherein the imaging head is configured to define a field of view, and wherein the field of view includes at least a distal end of the implant when the imaging head is in the retracted position,
wherein the handle is configured to selectively control movement of the imaging head, and
wherein the imaging head defines a support surface that is configured to support at least the distal portion of the implant.

20. A delivery device for deploying a self-expanding implant within a body cavity, the device comprising: at least one retention formation for holding the implant against axial or circumferential movement, wherein the at least one retention formation is fixed relative to a handle, and wherein an outer elongate element and an imaging head are moveable axially relative to the handle; an elongate longitudinally-extending outer element, radially outward of the at least one retention formation; and wherein the outer element is movable longitudinally relative to the at least one retention formation between: a storage position in which the outer element surrounds the implant and holds the implant engaged with the at least one retention formation; and a partial-deployment position in which the outer element uncovers a distal portion of the implant while surrounding a proximal portion of the implant to continue holding the implant engaged with the at least one retention formation; wherein the outer element is movable longitudinally, relative to the at least one retention formation, into a full-deployment position in which the outer element uncovers the proximal portion of the implant to an extent sufficient to disengage the implant from the retention formation for radial self expansion within the body cavity; and the handle configured to selectively control, disable and enable movement of the outer element into the full-deployment position.

21. The device of claim 20, wherein the handle comprises a detent.

22. The device of claim 21, wherein the detent is configured to selectively control movement of the outer element from the storage position into the partial-deployment position.

23. The device of claim 21, wherein the detent comprises a path and an extension configured to follow the path, the path comprising a detent range beyond which movement of the extension in a longitudinal direction is restricted, the extension movable beyond the detent range by deliberate relative movement between the extension and the path.

24. The device of claim 23, wherein the deliberate relative movement is in a second direction transverse to the longitudinal direction.

25. The device of claim 20, further comprising an imaging head disposed on a longitudinal axis that extends on a radially-inward side of the at least one retention formation, wherein the imaging head is movable longitudinally between:
an advanced position when the outer element is in the storage position; and
a retracted position when the outer element is in the partial-deployment position,
wherein the imaging head is configured to define a field of view, and wherein the field of view includes at least a distal end of the implant when the imaging head is in the retracted position.

26. The device of claim 25, wherein the handle is configured to selectively control movement of the imaging head.

27. The device of claim 20, wherein the at least one retention formation comprises a proximal protrusion and a distal protrusion defining a slot between them for at least partially receiving the implant.

28. The device of claim 20, further comprising an imaging head disposed on a longitudinal axis that extends on a radially-inward side of the at least one retention formation, wherein the imaging head is movable longitudinally between:
- an advanced position when the outer element is in the storage position; and
- a retracted position when the outer element is in the partial-deployment position, wherein the imaging head is configured to define a field of view, and wherein the field of view includes at least a distal end of the implant when the imaging head is in the retracted position, wherein the handle is configured to selectively control movement of the imaging head, and wherein the imaging head defines a support surface that is configured to support at least the distal portion of the implant.

29. A delivery device for deploying a self-expanding implant within a body cavity, the device comprising:
- at least one retention formation for holding the implant against axial or circumferential movement;
- an elongate longitudinally-extending outer element, radially outward of the at least one retention formation; and
- wherein the outer element is movable longitudinally relative to the at least one retention formation between:
  - a storage position in which the outer element surrounds the implant and holds the implant engaged with the at least one retention formation; and
  - a partial-deployment position in which the outer element uncovers a distal portion of the implant while surrounding a proximal portion of the implant to continue holding the implant engaged with the at least one retention formation;
- wherein the outer element is movable longitudinally, relative to the at least one retention formation, into a full-deployment position in which the outer element uncovers the proximal portion of the implant to an extent sufficient to disengage the implant from the retention formation for radial self expansion within the body cavity;
- a handle configured to selectively control, disable and enable movement of the outer element into the full-deployment position; and
- an imaging head disposed on a longitudinal axis that extends on a radially-inward side of the at least one retention formation, wherein the imaging head is movable longitudinally between:
  - an advanced position when the outer element is in the storage position; and
  - a retracted position when the outer element is in the partial-deployment position, wherein the imaging head is configured to define a field of view, and wherein the field of view encompasses at least a distal end of the implant when the imaging head is in the retracted position, wherein the handle is configured to selectively control, disable and enable movement of the imaging head, and wherein the imaging head defines a support surface that is configured to support at least the distal portion of the implant.

30. The device of claim 29, wherein the handle comprises a detent.

31. The device of claim 30, wherein the detent is configured to selectively control movement of the outer element from the storage position into the partial-deployment position.

32. The device of claim 30, wherein the detent comprises a path and an extension configured to follow the path, the path comprising a detent range beyond which movement of the extension in a longitudinal direction is restricted, the extension movable beyond the detent range by deliberate relative movement between the extension and the path.

33. The device of claim 32, wherein the deliberate relative movement is in a second direction transverse to the longitudinal direction.

34. The device of claim 29, wherein the at least one retention formation comprises a proximal protrusion and a distal protrusion defining a slot between them for at least partially receiving the implant.

* * * * *